(12) United States Patent
Kasabov

(10) Patent No.: US 9,002,682 B2
(45) Date of Patent: Apr. 7, 2015

(54) DATA ANALYSIS AND PREDICTIVE SYSTEMS AND RELATED METHODOLOGIES

(76) Inventor: Nikola Kirilov Kasabov, Auckland (NZ)

( * ) Notice: Subject to any disclaimer, the term of this patent is extended or adjusted under 35 U.S.C. 154(b) by 0 days.

(21) Appl. No.: 13/088,306

(22) Filed: Apr. 15, 2011

(65) Prior Publication Data

US 2011/0307228 A1 Dec. 15, 2011

Related U.S. Application Data

(63) Continuation of application No. PCT/NZ2009/000222, filed on Oct. 15, 2009.

(60) Provisional application No. 61/105,742, filed on Oct. 15, 2008.

(30) Foreign Application Priority Data

Oct. 15, 2008 (NZ) ........................... 572036

(51) Int. Cl.
| | | |
|---|---|---|
| *G06F 17/10* | (2006.01) | |
| *G06F 7/60* | (2006.01) | |
| *G06N 99/00* | (2010.01) | |
| *G06F 19/24* | (2011.01) | |
| *G06Q 10/04* | (2012.01) | |
| *G06F 19/18* | (2011.01) | |

(52) U.S. Cl.
CPC .............. *G06N 99/005* (2013.01); *G06F 19/24* (2013.01); *G06Q 10/04* (2013.01); *G06F 19/18* (2013.01)

(58) Field of Classification Search
CPC ......... G06F 19/08; G06F 19/24; G06F 19/34; G06F 19/3443; G06F 19/3481; G06F 19/30; G06F 19/32; G06F 19/70; G06N 99/005; G06Q 10/04
USPC .......................................................... 703/2
See application file for complete search history.

(56) References Cited

U.S. PATENT DOCUMENTS

| | | | | |
|---|---|---|---|---|
| 7,805,388 | B2 * | 9/2010 | Weston et al. ................... | 706/20 |
| 2006/0293817 | A1 * | 12/2006 | Hagiwara et al. ................ | 701/40 |
| 2010/0023307 | A1 * | 1/2010 | Lee et al. ........................ | 703/7 |

FOREIGN PATENT DOCUMENTS

| | | |
|---|---|---|
| WO | WO 2008/067551 | 6/2008 |
| WO | WO 2008/086002 | 7/2008 |

(Continued)

OTHER PUBLICATIONS

Song et al., TWNFI—a transductive neuro-fuzzy inference system with weighted data normalization for personalized modeling, 2006, 6 pages.*

(Continued)

*Primary Examiner* — Kamini S Shah
*Assistant Examiner* — Andre Pierre Louis
(74) *Attorney, Agent, or Firm* — Knobbe Martens Olson & Bear LLP

(57) ABSTRACT

A method, computer system, and computer memory medium optimizing a transductive model Mx suitable for use in data analysis and for determining a prognostic outcome specific to a particular subject are disclosed. The particular subject may be represented by an input vector, which includes a number of variable features in relation to a scenario of interest. Samples from a global dataset D also having the same features relating to the scenario and for which the outcome is known are determined. In an embodiment, a subset of the variable features within a neighborhood formed by the samples are ranked in order of importance to an outcome. The prognostic transductive model is then created based, at least in part, on the subset, the ranking, and the neighborhood. The subset and the neighborhood are then optimized until the accuracy of the transductive model is maximized.

15 Claims, 16 Drawing Sheets

(56) References Cited

FOREIGN PATENT DOCUMENTS

| WO | WO 2008/136995 | 11/2008 |
| WO | WO 2009/052559 | 4/2009 |
| WO | WO 2009/158215 | 12/2009 |

OTHER PUBLICATIONS

International Search Report for International Patent Application No. PCT/NZ2009/000222, dated Feb. 23, 2010.

* cited by examiner

FIG. 2

| $V_x$ | $W_1$ | $W_2$ | ... | $W_v$ | $K_x$ | $s_1$ | $s_2$ | ... | $s_k$ | $M_x$ | $p_1$ | $p_2$ | ... | $p_m$ |

DATA ANALYSIS AND PREDICTIVE SYSTEMS AND RELATED METHODOLOGIES

CROSS-REFERENCE TO RELATED APPLICATIONS

This application is a continuation application, and claims the benefit under 35 U.S.C. §§120 and 365 of PCT Application No. PCT/NZ2009/000222, filed on Oct. 15, 2009, which is hereby incorporated by reference. PCT/NZ2009/000222 also claimed priority from New Zealand Patent Application No. 572036, filed on Oct. 15, 2008, which is hereby incorporated by reference. PCT/NZ2009/000222 also claimed priority U.S. Patent Application No. 61/105,742, filed on Oct. 15, 2008, which is hereby incorporated by reference.

BACKGROUND

1. Field

The described technology relates to data analysis and predictive systems and related methodologies. In particular the described technology relates to customised or personalised data analysis and predictive systems and related methodologies.

2. Description of Related Technology

The concept of personalised medicine has been promoted widely in the recent years through the collection of personalised databases, establishment of new journals and new societies and publications in international journals (see for example ref 1-7). Despite the furore of interest in this area, there are at present no adequate data analysis methods and systems which can produce highly accurate and informative personalised models from data.

Contemporary medical and other data analysis and decision support systems use predominantly inductive global models for the prediction of a person's risk, or likely outcome of a disease for an individual. In US20050131847A1, for example, features are pre-processed to minimise classification error in a global Support Vector Machine model used to identify patterns in large databases. Pre-processing may be performed to constrain features used to train the global SVM learning system. Global modelling in general is concerned with deriving a global formula (e.g. via regression, a "black box neural network", or a support vector machine) from the personal data of many people. The global formula is expected to perform well on any new subject, at any time, anywhere in world. Based on this expectation, drugs may be designed to target a disease, and these drugs are assumed to be useful for everybody who suffers from this disease. When a global model is created, a set of features (variables) may usually be selected that applies to the whole problem space (e.g., all samples in the available data). However, statistics have shown very clearly that drugs developed by such global models will only be effective for around average of 70% of people in need of treatment, leaving a relatively large number of patients who will not benefit at all from treatment with the drug. With aggressive diseases such as cancer, any time wasted, e.g. either a patient not being treated, or being treated, with an ineffective treatment, can be the difference between life and death. In particular, it would be useful to determine from a sample taken from a patient (e.g. blood sample, tissue, clinical data and/or DNA) into what category a patient falls. This information can also be used to determine and develop treatments that will be effective at treating the remainder of the population.

It would therefore be useful if there could be provided data analysis methodologies and systems, which based on available population data, are capable of creating models which are more useful and informative for analysing and/or assessing an individual person for a given problem. Such models should also ideally achieve a higher degree of accuracy of prediction of outcome or classification than conventional systems and methodologies.

A step towards personalised medicine and profiling may be the creation of global models, that cover a whole population of data, but importantly comprise many local models, each of them covering a cluster (neighbourhood) of similar data samples (vectors) Such models are called local learning models. Such models may be adaptive to new data. Once created, a person's information can be submitted and a personal profile extracted in terms of the closest local model which may be based on the neighbourhood of vectors in the dataset closest to that of subject person. Such models include evolving connectionist systems (ECOS), such as those previously developed, patented and published (Kasabov 2000, 2002 and 2007). These methods identify groups (clusters or neighbourhoods) of similar samples and develop a local model for each cluster through a machine learning algorithm, collectively all clusters cover the whole problem space. While local learning models have been very useful to adapt to new data and discover local information and knowledge, these methods do not select specific subsets of features and precise neighbourhood of samples for a specific individual that would be required for a true personalised modeling, for example in personalised medicine.

While inductive modeling results in the incremental creation of a global model where new, unlabeled data may be "mapped" through a recall procedure, transductive inference methods (transductive models) estimate the value of a potential model (function) only in a single point of the space (e.g., that of the new data vector) and utilise the information (features) of samples close in space (e.g., related to this point). This approach seems to be more appropriate for clinical and medical applications, where the focus may be not so much on the model, but more on the individual patient. The focus may be on the accuracy of prediction for any individual patient as opposed to the global error associated with a global model which merely highlights the shortcomings of an inductive approach. Thus, with a transductive approach each individual data vector (e.g. a patient in any given medical area) obtains a customised, local model, that best fits the new data, rather than a global model, where new data may be matched to a model (formula) averaged for the whole dataset which fails to take into account specific information peculiar to individual data samples. Thus a transductive approach seems to be a step in the right direction when looking to devise personalized modelling useful in personalized medicine.

The general principle of transductive modeling can be stated as the following: for every new input vector x, that needs to be processed for a classification or a prognostic task, the closest K samples, that form a new sub-data set Dx, may be derived from an existing global data set D. A new model Mx may be dynamically created from these samples. The system may then be used to calculate the output value y for this input vector x (Vapnik 1998).

A simple and classical transductive inference method may be the K-nearest neighbour method (K-NN) where the output value y for a new vector x may be calculated as the average of the output values of the K-nearest samples from the data set Dx. In a weighted K-NN method (WKNN) the output y may be calculated based on the weighted distance of the K-NN samples to x:

$$y = (\Sigma_{j=1,K}(w_j y_j))/(\Sigma_{j=1,K}(w_j)) \qquad (1)$$

where: y is the output value for the sample x from Dx; $y_j$ is the output value for the sample $x_j$ in the neighbourhood of x; $w_j$ is the weighted distance between x and $x_j$ measured as:

$$w_j = \max(d) - [d_j - \min(d)]. \quad (2)$$

In Eq. (2), the vector distance $d = [d_1, d_2, \ldots, d_K]$ may be defined as the distances between the new input vector x and the nearest samples $(x_i, y_j)$ for $j = 1$ to K; max(d) and min(d) are the maximum and minimum values in d respectively.

In general, distance between two q-element vectors x and z of same variables may be measured as normalised Euclidean distance defined as follows:

$$d_{x,z} = \mathrm{SQRT}(\Sigma_{l=1 \text{ to } q}(x_l - z_l)^2)/q \quad (3)$$

In another classification method, called WWKNN, not only may the nearest samples be weighted based on their distance to the new sample x, but the contribution of each of the variables may be weighted based on their importance for the nearest neighbor area of x (Kasabov 2007).

The KNN, WKNN and WWKNN methods use a single formula to calculate the output y for the input vector x based on the K nearest neighbours. These methods do not suggest how to select the number K and the most suitable set of K nearest samples, neither they suggest how to select the number of variables V, that would give the best accuracy of each personalised model Mx. By way of contrast these methods use a fixed number of K nearest neighbours and a fixed number of variables.

Other methods create a machine learning model from the K nearest neighbours and the model may then be used to calculate the output y. Such methods for example are: Transductive Neural Fuzzy Inference System—NFI and Transductive Neural Fuzzy Inference System with Weighted Data Normalization—TWNFI (Song and Kasabov 2006). As the above group of methods, these methods do not suggest how to select the number K of nearest samples, neither they suggest how to select the number of variables V, that would give the best accuracy of the personalised model Mx.

To summarise, in the above transductive methods, there is no efficient method for personalised feature selection (e.g. features such as important genes, clinical and/or other variables) required for personalised prognosis, classification, profiling, and/or treatment selection. These transductive methods also do not rank variables (features) in terms of importance form person and for an optimal personal model creation based on these variables and a personalised selection of the nearest neighbour samples from the available data set. There is also no methodology to suggest how individual scenarios for personal improvement (e.g. treatment) can be designed.

SUMMARY OF CERTAIN INVENTIVE ASPECTS

Disclosure of Invention

According to an aspect of the described technology a computer implemented method of optimising a model Mx suitable for use in data analysis and determining a prognostic outcome specific to a particular subject (input vector x), the subject comprising a number of variable features in relation to a scenario of interest for which there is a global dataset D of samples also having the same features relating to the scenario, and for which the outcome is known is provided; the method comprising:

a) determining what number and which variables (features) Vx will be used in assessing the outcome for the input vector x;

b) determining what number Kx of samples from within the global data set D will form a neighbourhood about x;

c) selecting Kx samples from the global data set which have the variable features that most closely accord to the variable features of the particular subject x to form the neighbourhood Dx;

d) ranking the Vx variable features within the neighbourhood Dx in order of importance to the outcome of vector x and obtaining a weight vector Wx for all variable features Vx;

e) creating a prognostic model Mx, having a set of model parameters Px and the other parameters from elements a)-d);

f) testing the accuracy of the model Mx at element e) for each sample from Dx;

g) storing both the accuracy from element f), and the model parameters developed in elements a) to e);

h) repeating elements a) and/or b) whilst applying an optimisation procedure to optimise Vx and/or Kx, to determine their optimal values and the corresponding sets, before repeating elements c)-h) until maximum accuracy at element f) is achieved.

According to another aspect of the described technology a method as described above is provided which includes:

i) calculating the outcome y for the input vector x using the optimised model Mx created at element h).

According another aspect of the described technology a method substantially as described above is provided which includes:

j) profiling input vector x and comparing important variable features against important variable features associated with a desired outcome to provide for, or assist with, development of, scenarios for improvement of the outcome for input vector x.

According another aspect of the described technology a computer implemented method of determining a profile of a subject (input vector x) based on a model Mx and for recommending changes to the profile in relation to a scenario of interest in order to improve the outcome for input vector x is provided comprising:

(I) creating a personalised profile of input vector x;

(II) comparing each important variable feature of input vector x to the average value of each important variable feature of samples having the desired outcome; and (III) determining which important variable features of input vector x can be altered in order to improve the outcome.

It is desirable in certain embodiments that the determination of which variables should be changed will take into account the weight vector Wx of the variable. It is desirable in certain embodiments that the variables that will be changed will be those which may be important with respect to the outcome.

The term 'personalised profile' as used herein refers to an input vector and to the predicted outcome for that vector.

According another aspect of the described technology a system is provided which includes:

a processor and associated memory (herein collectively the hardware);

the system characterized in that the hardware has been programmed to:

access a global dataset of samples relating to a scenario of interest, and for which the outcome is known, each sample having a number of variable features, which may or may not relate to the scenario;

receive input information relating to an input vector x; and to perform a method substantially as described above.

A computer memory medium which contains a program which is capable of performing a method as described above on a global dataset of samples for which the outcome is known relating to a scenario of interest, each sample having a number of variable features, which may or may not relate to the scenario; and wherein the program provides for an user interface to receive input information relating to an input vector x and wherein the program also provides for graphic display of the method results.

An embodiment of the proposed method and system of optimising a model Mx suitable for use in data analysis and determining a prognostic outcome may include the following modules as shown in FIG. 1):

- Module for most relevant features (variables) Vx selection and their ranking Wx by importance for x;
- Module for the selection of a number Kx of neighbouring samples of x and for the selection of neighbouring samples Dx;
- Module for a prognostic model Mx creation, defined by the model parameters Px and the parameters including Kx, Vx, Dx which were derived in the previous modules;
- Module for a final output y calculation for x, for personalised profiling; and
- Module for the design of scenarios for improvement.

The described technology has utility in relation to a wide variety of scenarios of interest in areas as diverse as meteorology, drug development, bioinformatics, personalized medicine, psychological profiling, nutri-genomics, finance and economics, to name but a few.

For ease of reference only the described technology will now be discussed in relation to personalized medicine, however, this should not be seen as limiting.

The variable features, also referred to as simply variables or features, may be any piece(s) of information that one has collected in relation to samples forming a global dataset relating to a scenario of interest. In personalized medicine applications of the described technology the variable features may relate to the different genes of patients implicated in a disease or disorder, clinical data, age, gender. In fact the variable features may be almost information that has been collected from or about the patients in the dataset which may be of relevance to the disease of interest.

We assume that the scenario of interest (e.g., the problem which is to be analysed) is either:

- Classification—For simplicity we can assume two classes of outcome (e.g., output values) for an input vector (e.g., class 1 (survive a disease after treatment), and class 2 (die of disease after treatment)). However, it will be appreciated that the described technology is also applicable to multiple class classification problems; or
- Risk evaluation and prediction—where the output values assigned to the samples are continuous values. For example: renal function evaluation measured as GFR; cardio-vascular risk measured in probability of an event to happen; for example the risk of diabetes.

The described technology assumes that there is a global data set D (or multiple data sets) of individual records (samples) $S_i=(x_i, y_i)$, $i=1, 2, \ldots, N$. There is also a new input vector x for which an output value (outcome) y is to be calculated.

The variables in the data set D partially or preferably fully overlap with the variables in the new input vector x. If it is a partial overlap, a common variable set of q variables in D and x is determined and a new data set is created as a subset of D. Initially, it is assumed that all variables have equal absolute and relative importance for x in relation to predicting its unknown output y:

$$w_{v1}=w_{v2}=\ldots=w_{vq}=1; \quad (4)$$

and $$w_{v1,norm}=w_{v2,norm}=\ldots=w_{vq,norm}=1/q; \quad (5)$$

The numbers initially determined for Vx and Kx at steps a) and b) may be determined in a variety of different ways without departing from the scope of the present invention.

In preferred embodiments the number for Vx (Step a) and/or Kx (Step b) may be initially determined (e.g., prior to iteration of the method steps as per step h)) following an assessment of the global dataset in terms of size and/or distribution of the data. Minimum and maximum values of these parameters may also be established a priori based on the data available and the problem. For example, Vx_min=3 (minimum three variables used in a personalised model) and Vx_max<Kx (the maximum variables used in a personalized model is not larger than the number of samples in the neighbourhood Dx of x), usually Vx_max<20. The initial set of variables may include expert knowledge, e.g., variables which are referenced in the literature as highly correlated to the outcome of the problem (disease) in a general sense (over the whole population). Such variables are the BRCA genes, when the problem is predicting outcome of breast cancer (van Veer et al, 2002). For an individual patient the BRCA genes may interact with some other genes, which interaction will be specific for the person or a group of persons and may be likely to be discovered through local or/and personalized modeling only (Kasabov et al, 2005).

The present invention, when compared with global or local modeling, may start the modeling process with all relevant variables available for a person, rather than with a fixed set of variables in a global model that may well be statistically representative for a whole population, but not necessarily representative for a single person in terms of optimal model and best profiling and prognosis for this person.

Selecting the initial number for Kx and also the minimum and the maximum numbers Kx_min and Kx_max will also depend on the data available and on the problem in hand. A general requirement is that Kx_min>Vx, and, Kx_max<cN, where c is for example 0.5. Several formulas have been already suggested and experimented (Vapnik, 1998; Mohan and Kasabov, 2005), for example:

- Kx_min equals the number of samples that belong to the class with smaller number of samples when the data is imbalanced (one class has many more samples, e.g. 90%, than the another class) and the available data set D is of small or medium size (e.g., hundreds to few thousands samples);
- Kx_min=SQRT (N), where N is the total number of samples in the data set D.

A subsequent iterations of method steps a) and b) the Vx and Kx parameters may be optimized pursuant to step h) via an optimization procedure such as is outlined further below.

At step h) the optimization procedure(s) which can be employed with the method and system of the described technology may include three alternative methods and/or a combination of the methods set out below:

1. An exhaustive search, where all or some possible values of the all or some of the parameters Vx, Wx, Kx, Mx and Px (see FIG. 2) within their constraints, are used in their combination and the model Mx with the best accuracy is selected.

2. A genetic algorithm (GA) may be used (Goldberg 1989) to optimize all or some parameters from the "chromosome" (FIG. 2), Genetic algorithms (GA) are methods that have been used to solve complex combinatorial and organizational problems with many variants, by employing analogy with Nature's evolution. Genetic algorithms were introduced for the first time in the work of John Holland (Holland 1975). They were further developed by him and other researchers (Goldberg 1989).

The most important terms used in a GA are analogous to the terms used in biology in relation to the study of Genetics. They are:

gene—a basic unit, which defines a certain characteristic (property) of an individual. In case of FIG. 2, "genes" are the parameters and variables to be optimized for a personalized model Mx.

chromosome—a string of genes; it is used to represent an individual, or a possible solution to a problem in the solution space (see FIG. 2).

population—a collection of individuals—in our case it is a population of chromosomes each one representing one personalised model for the new input vector x.

crossover (mating) operation—a set of different models is taken and a new set of models is produced, e.g. from two models, each represented by a chromosome, new ones are generated through combining parts of the first model chromosome (mother) and parts from the other (father).

mutation—random change of a gene (variable) in a chromosome.

fitness (goodness) function—a criterion which evaluates how good each individual is. In our case it will be the accuracy Ax of the model (or the error Ex).

selection—a procedure of choosing a part of the population which will continue the process of searching for the best solution, e.g. the 10 best models.

The steps in a GA are:

Generate initial population of individuals (personalised models)—each individual defined as a chromosome containing parameters—genes (This is done in Steps a and b as explained in the invention).

Evaluate the fitness of each individual (the accuracy of each model) using a fitness function (accuracy of the model Ax). In our case this is done in Step f.

Select a subset of individuals based on their fitness (This is done is Step h.

Apply a crossover procedure on the selected individuals to create a new generation of a population h Apply mutation h Continue with the previous procedure h until a desired solution (with a desired fitness) is obtained, or the run time is over.

Genetic algorithms comprise a great deal of parallelism. Thus, each of the branches of the search tree for best individuals can be utilized in parallel with the others. This allows for an easy realization of the genetic algorithms on parallel architectures.

Selection of the best models to continue the process of optimization is based on fitness. A common approach is proportional fitness (roulette wheel selection), e.g., if a model Mx is twice as good as another one, its probability of being selected for the crossover process is twice higher. Roulette wheel selection gives chances to individuals according to their fitness evaluation (see example below (from Kasabov, 2007).

Important feature of the selection procedure is that fitter individuals (models Mx with higher accuracy) are more likely to be selected.

The selection procedure can involve also keeping the best individuals from the previous generation. This operation is called elitism.

After the best individuals are selected from a population of models, a cross over operation is applied between these individuals. Different cross-over operations can be used:
one-point cross-over;
three-point cross over (as shown in FIG. 8 from Kasabov, 2007), or more.

Mutation can be performed in the following ways:
For a binary string, just randomly 'flip' a bit.
For a more complex "genes" and "chromosomes", randomly select a gene an change its value.

Some GA methods just use mutation (no crossover, e.g. evolutionary strategies). Normally, however, mutation is used to search in a "local search space", by allowing small changes in the "genotype" (and therefore hopefully in the "phenotype").

In other implementations of the proposed in the invention method and system other evolutionary computation algorithms can be used for the optimization of the parameters of a personalized model (FIGS. 1, 2), such as evolutionary strategies (Kasabov, 2007).

While GA have been used in some previously developed methods for model optimization, e.g.: NeuCom and ECF parameter and feature optimization for local modeling; model and parameter optimization of global models (Sureka, 2008); basic parameter and feature optimization for personalised models (Mohan and Kasabov, 2005), GA and the other evolutionary optimization techniques have never been used for the integrated optimization of features V, feature weights W, number of nearest neighbours K, models M and their parameters P related to personalised modeling.

Step c) goes on to find the closest Kx neighboring samples to x from D and forms a new data set Dx. Preferably, step c) uses a novel distance measure which is a local weighted variable distance measure that weighs the importance of each variable $V_l$ (l=1, 2, . . . , q) to the accuracy of the model outcome calculation for all samples in the neighbourhood Dx using a classification or prediction model. For example, the distance between x and another sample z from Dx may be measured as a local weighted variable distance:

$$d_{x,z}=\text{SQRT}(\Sigma_{l=v1\ to\ vq}((1-w_{l,norm})(x_l-z_l)^2))/q \qquad (6)$$

where: $w_l$ is the weight assigned to the variable $V_l$ and its value is calculated as:

$$w_{l,norm}=w_l/\Sigma_{l=1\ to\ q}(w_l) \qquad (7)$$

The above formulas (6) and (7) are different from the traditionally used one (3) and this is the basis of a novel supervised neighbourhood clustering method proposed here, where the distance between a cluster centre (in our case it is the vector x) and cluster members (neighborhood samples from Dx) is calculated not only based on the geometrical distance, as it is in the traditional unsupervised clustering methods, but on the relative importance weight vector Wx for the output values of all samples in the neighborhood Dx.

After a subset Dx of Vx variables and Kx samples is selected in step c), the variables are ranked at step d) in a descending order of their importance for prediction of the output y of the input vector x and a weighting vector Wx obtained. Through an iterative optimization procedure explained below the number of the variables Vx to be used for an optimized personalized model Mx will be reduced, selecting only the most appropriate variables that will provide the best personalized prediction accuracy of the model Mx. For the weighting Wx (e.g., ranking) of the Vx variables, the following alternative methods can be used:

(i) In one implementation, applicable to a classification task, calculate Wx as normalised SNR (Signal-to-Noise Ratio) coefficients (or another ranking coefficients, such as t-test, or p-value) and sort the variables in descending order: V1, V2, . . . , Vv, where: $w_1 >= w_2 >= \ldots >= w_v$, calculated as follows:

$$w_l = abs(M_l^{(class\ 1,x)} - M_l^{(class\ 2,x)})/(Std_l^{(class1)} + Std_l^{(class2)}) \quad (8)$$

Here $M_l^{(class\ s)}$ and $Std_l^{(class\ s)}$ are respectively the mean value and the standard deviation of variable $x_l$ for all vectors in Dx that belong to class s.

This method is very fast, but evaluates the importance of the variables in the neighborhood Dx one by one and does not take into account a possible interaction between the variables that might affect the model output.

(ii) In another implementation, applicable to both classification and prediction tasks, for all variables Vx all possible combinations of values of their weights Wx are tested through an exhaustive search to maximize the overall accuracy of a model built on the data Dx. For example, each variable weight $w_l$ can take values from 0 to 1 with a step of 0.2. In this case, the number of the tests will be $6^{Vx}$, which for small number of variables is operational but for a large number of variables is very time consuming and not practical. This is an exhaustive search method for the optimization of the variable weights Wx in regard to the model output for all samples from Dx.

(iii) In a third implementation, applicable if the number of variables prevents using method (ii) above, a faster optimization method can be used instead of the exhaustive search of all possible combinations as in (ii). Such method is for example the GA (as explained above).

(iv) In a fourth implementation, another evolutionary algorithm—quantum inspired evolutionary algorithm, is used to select the optimal variable set Vx for every new input vector x and to weigh the variables through probability wave function as in (Defoin-Platel, Schliebs, Kasabov, 2007 and 2008).

At step e) to create a prognostic model Mx a classification or prediction procedure is applied to the neigbourhood Dx of Kx samples to derive a personalized model Mx using the already defined variables Vx, variable weights and a model parameter set Px. At step f) a local accuracy error Ex, that estimates the personalised accuracy of the personalised prognosis (classification) for the data set Dx using model Mx is evaluated. This error is a local one, calculated in the neighborhood Dx, rather than a global accuracy, that is commonly calculated for the whole problem space D.

A variety of methods for calculating error can be employed such as.

A novel formula for calculating error which may be utilized in preferred embodiments of the present invention:

$$Ex = (\Sigma_{j=1,Kx}(1-d_{x,j})E_j)/Kx \quad (9)$$

where: $d_{x,j}$ is the weighted Euclidean distance between sample x and sample Sj from Dx that takes into account the variable weights Wx; $E_j$ is the error between what the model Mx calculates for the sample j from Dx and what its real output value is, for example; if the model Mx calculates for the sample Sj∈Dx an output of 0.3 and this is a classification problem where sample Sj's class is 0, the error will be 0 if a classification threshold of 0.5 is used; the error Ej will be 0.2 if the desired output for Sj is 0.1 and it is a risk prediction problem.

In the above formula, the closer a sample Sj to x is, based on a weighted distance measure, the higher its contribution to the error Ex. Distant samples from x in Dx do not contribute much to the local error Ex.

The calculated personalized model Mx accuracy at step f) is:

$$Ax = 1 - Ex \quad (10)$$

At step g) the best accuracy model obtained is stored for a future improvement and optimization purposes, It is envisaged that the described technology may employ any number of different classification or prediction procedures at step e) to create the model. These may preferably include methods that use weighted variables for the evaluation of an output value when an input vector is presented. Two, publicly available methods of this category are:

The weighted-weighted K-nearest neighbor method, WWKNN (Kasabov, 2007a,b);

The transductive, weighted neuro-fuzzy inference method TWNFI (Song and Kasabov, 2006)

but should in no way be restricted to them. Statistical methods, such as: linear regression method; logistic regression; support vector machine; nearest neighbour K-NN method; W-KNN method; and machine learning methods, such as: neural networks; fuzzy systems; evolving fuzzy neural network EFuNN (Kasabov, 2000, 2002, 2007) can also be used for some specific applications.

At step h) the method iteratively returns to all previous steps to select another set of parameter values for the parameter vector from FIG. 2 according to one of the four optimization procedures listed above (exhaustive search, genetic algorithm, quantum evolutionary algorithm, a combination between these three methods) until the model Mx with the best accuracy is achieved.

The method at step h) may in some preferred embodiments also optimize the classification procedure that is used by the method at step e) along with the parameters Px of said procedure.

The method at step h) may also preferably optimize any parameters Px of the classification/prediction procedure. These parameters Px may be optimized by an optimization procedure substantially as described above.

Once the best model Mx is derived at step h), at step i) an output value y for the new input vector x is evaluated using this model. For example, when using the WWKNN method, the output value y for the input vector x is calculated using the formula:

$$y = (\Sigma_{j=1,K}(a_j y_j))/(\Sigma_{j=1,K}(w_j)) \quad (11)$$

where: $y_j$ is the output value for the sample $x_j$ in the neighbourhood Dx of x and:

$$a_j = \max(d) - [d_j - \min(d)]. \quad (12)$$

In Eq. (16), the vector distance $d = [d_1, d_2, \ldots d_K]$ is defined as the distances between the new input vector x and the nearest samples $(x_j, y_j)$ for j=1 to K; max(d) and min(d) are the maximum and minimum values in d respectively. Euclidean distance $d_j$ between vector x and a neighboring one $x_j$ is calculated now as:

$$d_j = sqr[sum_{l=1\ to\ V}(w_l(x_l - x_{jl}))^2], \quad (13)$$

where: $w_l$ is the coefficient weighing variable $x_l$ in the neighbourhood Dx of x as per Step d).

When using the TWNFI classification or prediction model, the output y for the input vector x is calculated as follows:

$$y = \frac{\sum_{l=1}^{M} \frac{n_l}{\delta_l^2} \prod_{j=1}^{P} \alpha_{lj} \exp\left[-\frac{w_j^2(x_{ij}-m_{lj})^2}{2\sigma_{lj}^2}\right]}{\sum_{l=1}^{M} \frac{1}{\delta_l^2} \prod_{j=1}^{P} \alpha_{lj} \exp\left[-\frac{w_j^2(x_{ij}-m_{lj})^2}{2\sigma_{lj}^2}\right]} \quad (14)$$

Where: M is the number of the closest clusters to the new input vector x, each cluster l defined as a Gaussian function $G_l$ in a Vx dimensional space with a mean value $m_l$ as a vector and a standard deviation $\delta_l$ as a vector too; x=(x1,x2, ..., $x_v$); $\alpha_l$ (also a vector across all variables V) is membership degree to which the input vector x belongs to the cluster Gaussian function $G_l$; $n_l$ is a parameter of each cluster (see Song and Kasabov, 2006).

After the output value y for the new input vector x has been calculated at step i), at step j) a personalized profile Fx of the person represented as input vector x is derived, assessed against possible desired outcomes for the scenario, and possible ways to achieve an improved outcome can be designed.

In one implementation, a personal improvement scenario, consisting of suggested changes in the values of the persons' variable features to improve the outcome for x, according to method steps (I)-(III) below, may be designed as follows:

At step (I) The current person's x profile Fx may be formed as a vector:

$$F_x = \{Vx, Wx, Kx, Dx, Mx, Px, t\}, \quad (15)$$

where the variable t represents the time of the model Mx creation. At a future time (t+Δt) the person's input data x may change to x' (due to changes in variables such as age, weight, gene expression values, etc.), or the data samples in the data set D may be updated and new samples added. A new profile Fx' derived at time (t+Δt) may be different from the current one Fx.

At step (II) an average profile Fi for every class Ci in the data Dx (e.g. class 1—good outcome or a desired person's profile, class 2—bad outcome, non-desirable profile) may be created as follows:

$$Fi = \{(V_{1\_av\_class\_i}, V_{2\_av\_class\_i}, \ldots, V_{v\_av\_class\_i}), (w_1, w_2, \ldots, w_v)\} \quad (16)$$

where: $V_{l\_av\_class\_i} = \Sigma_{j=1,Nx\_class\_i}(V_{l\_j,i})/N_{x\_class\_i}$ (17)

where: $V_{l\_j,i}$ is the value of the variable $V_l$ for the sample j of class i in the data set Dx of $N_{x\_class\_i}$ neighbouring samples to x in Dx that belong to class Ci.

The importance of each variable feature is indicated by its weighting. The weighted distance from the person's profile Fx and the average class profile Fi (for each class i) may be defined as:

$$D(Fx, Fi) = \Sigma_{l=1,v} abs(V_{lx} - V_{li}) \cdot w_l \quad (18)$$

where: $w_l$ is the weight for the variable $V_l$ in the data set Dx.

Assuming that Fd is the desired profile (e.g. good outcome) the weighted distance D(Fx,Fd) may be calculated as an aggregated indication of how much a person's profile should change to reach the average desired profile Fd:

$$D(Fx, Fd) = \Sigma_{l=1,v} abs(V_{lx} - V_{ld}) \cdot w_l \quad (19)$$

At step (III) a scenario for a person's improvement through changes made to variable features towards the desired average profile Fd may be designed as a vector of required variable changes, defined as:

$$deltaFx, d = (deltaV_{lx,d})_{\text{for } l=1,v} \text{ as follows:} \quad (20)$$

$$deltaV_{lx,d} = V_{lx} - V_{ld}, \text{ with an importance of: } w_l \quad (21)$$

In any given scenario certain variable features of input vector x will automatically be, or can be manually, selected as being not capable of being altered in order to improve the outcome. One example of such a variable which can not generally be altered (e.g., targeted) to affect outcome may be age and another such variable feature may be gender.

Thus, example embodiments of the described technology may have a number of advantages, which can include among other things:

(i) Providing a more accurate prognosis for an individual input vector (a personal outcome) when compared with the use of already created local and global models;

(ii) Providing a unique personal profiling methodology and system and assisting with the design of possible improvement scenarios if necessary;

(iii) Providing an improved personalised model, in advance, or, when new feature variables for a person are available or new samples in the data are made available;

(iv) Providing a personalised model which can capture and explain, for an input vector x, specific interactions between feature variables that can provide a key for better personalised profiling and outcome prediction;

(v) Providing a methodology and system which can be applied to a wide range of scenarios where prediction of outcome is useful;

(vi) Providing an improved formula for calculating local error in predictive data analysis models.

(vii) Providing a procedure to select nearest neighbours of a vector x from a given data set, that procedure takes into account already defined personalised weights of importance for each variable.

BRIEF DESCRIPTION OF DRAWINGS

Further aspects of the described technology will become apparent from the following description which is given by way of example only and with reference to the accompanying drawings in which:

FIG. 2 shows diagrammatically the key parameters which are optimised and utilised in the present invention.

DETAILED DESCRIPTION OF CERTAIN INVENTIVE EMBODIMENTS

Figure 1:
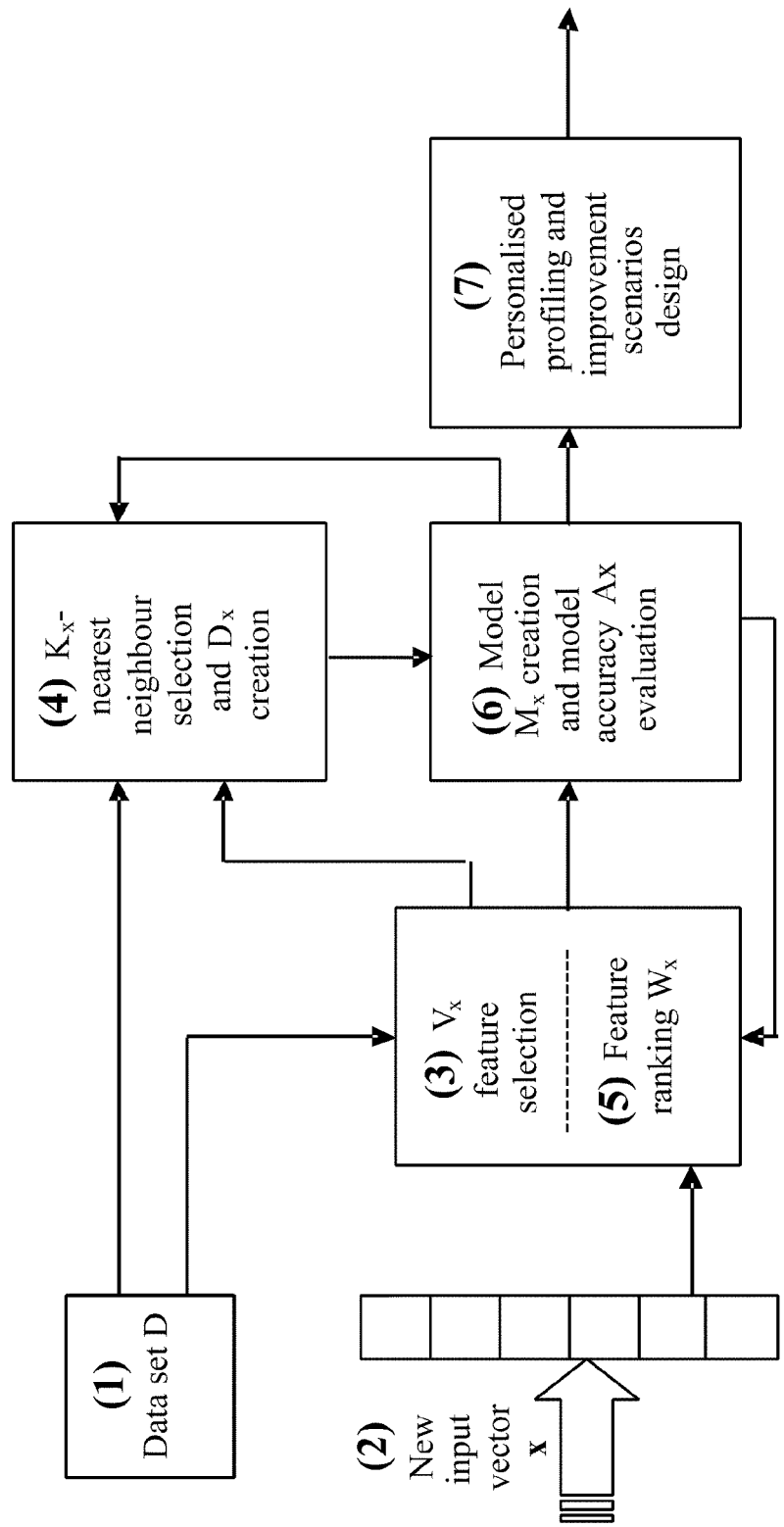
FIG. 1 shows a block diagram of the method which would be implemented by the system.

For ease of reference the described technology will now primarily be discussed in relation to an implementation for personalised medicine however this should not be seen as limiting. The described technology has applications in information science, mathematical modelling, personalised medicine, personalised drug design, personalized food design, profiling and prognostic systems for predicting outcomes, or evaluating risks, based on a dataset of information which includes information relating to past outcomes for a given scenario.

Thus, the described technology may be applied to a wide range of datasets for which there may be information relating to the composition of different data elements together with information as to the known outcome for an individual data element or combination of elements in relation to a scenario of interest.

An underlying philosophy behind the described technology is the realisation that every person is different, and therefore an individual ideally needs their own personalised model and tailored treatment. The implementation of this philosophy has now become more of a reality given the fact that more and more individual data for a person, e.g., DNA, RNA, protein expression, clinical tests, age, gender. BMI, socio factors, inheritance, foods and drugs intake, diseases, to name a few—are more readily obtainable nowadays, and are easily measurable and storable in electronic data repositories for a lesser cost.

The described technology includes a method and a system for the selection and ranking of important personal variables Vx related to an input vector x and a problem, for the selection of the most appropriate number of nearest neighbouring samples Kx and also the most appropriate nearest samples, for the creation of an optimal personalised prognostic model Mx. The described technology allows for the prediction of outcome, or for risk evaluation, in relation to an input vector x following the creation of the prognostic model Mx. The described technology can also be used for the design of personal improvement scenarios. The method of the described technology may be based on the use of a person's information x, that may include DNA, gene expression, clinical, demographic, cognitive, psychiatric data, and a comparison against this personal information from other people within a data set. The proposed general method iteratively selects the most important features (variables) Vx, ranks them through a weight vector Wx for the person in relation to the problem, selects the optimum number Kx of neighbours and selects the set Dx of neighbouring samples, creates a personalised prognostic model Mx with optimal parameters Px using the selected variables and nearest samples. These parameters, Vx, Wx, Kx, Dx, Mx, Px may be selected and optimised together, (e.g., in concert), so that the best accuracy of the personalised prognosis, or close to it may be achieved. This is a desirable aspect of the proposed method. Another desirable aspect of the method is a personalised profiling procedure in terms of defining variables that may need to be modified in a concert for the design of personal improvement scenarios afterwards, depending on the problem and the available resources. The method allows for an adaptation, monitoring and improvement of the personalised model should new data about the person or the population become available. Potential applications are in personalised medicine and personalised drug design for known diseases, (incl. cancer, cardiovascular disease, diabetes, renal diseases, brain disease, etc.), as well as for some other modelling problems in ecology, meteorology, sociology, crime prevention, business, finance, to name but a few.

All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, these references do not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—e.g., that it will be taken to mean an inclusion of not only the listed components it directly references, but also other non-specified components or elements. This rationale will also be used when the term 'comprised' or 'comprising' is used in relation to one or more steps in a method or process.

It is an object of the described technology to address the foregoing problems or at least to provide the public with a useful choice.

Further aspects and advantages of the described technology will become apparent from the ensuing description which is given by way of example only. FIG. 1 diagrammatically details the key method elements a)-i) in relation to a global data set D (1) relating to a scenario of interest and an input vector x (2) having a number of variables (3).

As per method elements a)-d) determine Vx and Kx than select the neighbourhood (4) then select, rank and optimize the most important variables Vx for a given individual input vector x and obtain a weight vector Wx of variable importance (5). Initially Vx variables may be treated as being equally important; however, in subsequent iterations of the method element s, the weighting vector Wx for each variable may be recalculated and optimized at element d). In addition subsequent interations of the method element s a)-d) seek to optimize Vx, Kx, Wx and the neighbourhood Dx. Further-more, in some preferred embodiments subsequent iterations of element e) may also seek to optimize the classification method used in the model Mx (6).

The creation of an optimized personalised model Mx for input vector x to predict the outcome of all samples from Dx, also involves an evaluation the accuracy of the model through calculating a local error Ex of the model Mx within Dx and the accuracy Ax is recalculated as part of the iterative application of the elements above.

Figure 2:
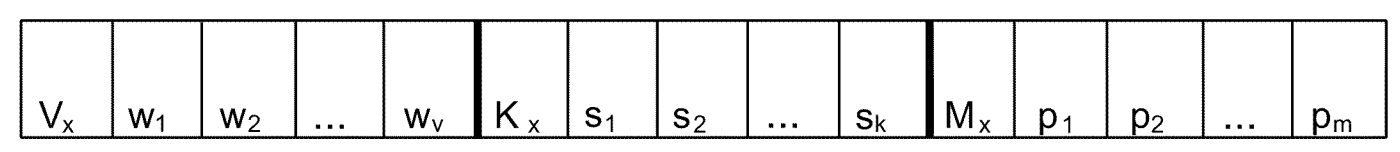

In FIG. 2 all, or two or more of the parameters, Vx, Wx, Kx, Dx, Mx, Px may be selected and optimized individually or together, (e.g., in concert), so that the best accuracy of prognosis, or a close to it, is achieved.

After finalising the model Mx, the output y=Mx(x) for the personal input vector x is calculated (7), a profile of the individual represented by x in regard to possible outcomes is created. If necessary, improvement scenarios may be designed, consisting of suggested changes in the values of the selected personalised feature variables as a concert taking into account their ranking, to improve the outcome.

The below Examples generally illustrate implementation of the methodology and systems of the present invention.

Example 1

Classifying Rock Versus Mine Based on the Reflection of Sonar Signal

This may be a standard bench mark data net available from the Machine learning repository of UC Irvine: (http://archive.ics.uci.edu/ml/datasets/Connectionist+ Bench+%28Sonar%2C+Mines+vs.+Rocks%29).

The data set was contributed to the benchmark collection by Terry Sejnowski, now at the Salk Institute and the University of California at San Diego. The data set was developed in collaboration with R. Paul Gorman of Allied-Signal Aerospace Technology Center.

The data contains 208 samples classified in two classes—rock vs mine based on 60 variables, continuous value between 0 and 1—reflections of a sonar signal from the objects (mine or rock) in different frequency bands. The task is to classify any new input vector of 60 or less such variables into one of the two classes—rock or mine. While a global approach of using one neural network of the type of a multilayer perceptron and a backpropagation learning algorithm results in 85% accuracy of classifying new samples, here we demonstrate that the proposed personalized modeling method achieves 94% accuracy and reveals more individual information about new objects.

To demonstrate the method a sample x may be randomly selected (this is sample #180) and a personalized model is built to classify this sample following the elements from the invention:

Element a) Vx=3 to 30.
Element b): Kx=20, . . . , 50.
Element c) A neighbourhood data set Dx of Kx samples is selected from all 207 samples;
Element d): For each number of variables V=3 to 30 the variables are weighted using a normalized SNR method to obtain the weight vector Wx;
Element e): A model Mx is created using the KNN method, here applied on a larger number of variables (60). The only parameter P of the KNN model that can be optimized as part of the optimization vector FIG. 2 is the classification threshold. Here it is assumed to be fixed at 0.5.

Element f and g) The local accuracy is evaluated using formulas (9-11) and stored.

Element h): The above elements are repeated in an exhaustive search mode and the best model and its accuracy are recorded which is given below:

Kx=50 neighbors;

Dx=(179 190 191 55 195 56 41 188 94 194 189 140 192 93 95 163 193 64 57 54 208 178 42 205 38 31 196 204 203 60 207 61 50 62 59 206 183 199 53 181 58 28 173 198 200 39 49 184 10 121)

The best local accuracy on training data is 94.00%.

Figure 3:
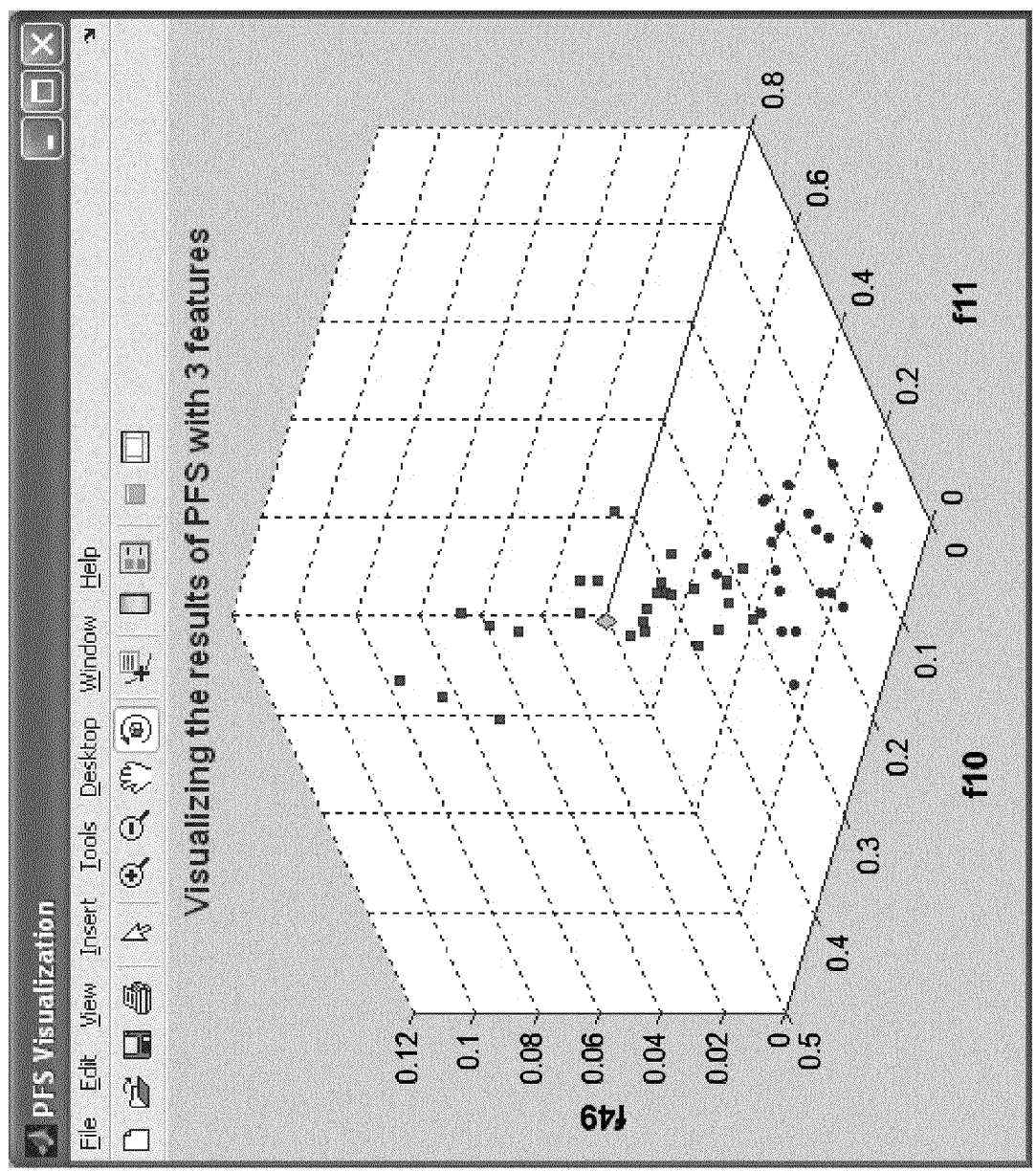
FIG. 3 shows the selected neighbourhood area Dx of 50 samples around a sample #180 (represented as a diamond) in the 3D space of the top three ranked variables V11, V10 and V49 (out of 14) for the best personalised classification model related to classifying samples belonging to two classes—rocks and mines, from a standard bench mark data set explained in Example 2.

The best selected number of variables is Vx=14, which are weighted using 50 neighbouring samples of x. The neighbourhood area Dx is shown in FIG. 3 in the space of the top three variables V11, V10 and V49.

Here is the weight vector Wx of the 14 features, evaluated using the SNR method (formula (8)) and then the SNR values are normalized across all features (formula (5)):

| Feature # | Weighted SNR value |
|---|---|
| 11 | 0.1048 |
| 10 | 0.0897 |
| 49 | 0.0878 |
| 48 | 0.0809 |
| 51 | 0.0769 |
| 36 | 0.0769 |
| 47 | 0.0746 |
| 12 | 0.0721 |
| 9 | 0.0679 |
| 35 | 0.0637 |
| 46 | 0.0580 |
| 28 | 0.0510 |
| 52 | 0.0483 |
| 27 | 0.0474 |

Element i): Calculating the output y for x and profiling:
Calculating the output for x:

| sample # | output | predicted class | actual class |
|---|---|---|---|
| 180 | 1.64 | 2 | 2 |

Profiling of sample 180 is done as explained in the description of Element j of the invention, using formula (16):

| Feature | Mean Value(Cls1) | Mean Value(Cls2) | Sample 180's Value |
|---|---|---|---|
| 11 | 0.1747 | 0.2896 | 0.3078 |
| 10 | 0.1593 | 0.2510 | 0.2558 |
| 49 | 0.0384 | 0.0637 | 0.0588 |
| 48 | 0.0695 | 0.1106 | 0.0969 |
| 51 | 0.0123 | 0.0194 | 0.0118 |
| 36 | 0.4607 | 0.3186 | 0.2897 |
| 47 | 0.0945 | 0.1469 | 0.0766 |
| 12 | 0.1916 | 0.3015 | 0.3404 |
| 9 | 0.1374 | 0.2135 | 0.1618 |
| 35 | 0.4555 | 0.3376 | 0.3108 |
| 46 | 0.1169 | 0.1988 | 0.0566 |

| Feature | Mean Value(Cls1) | Mean Value(Cls2) | Sample 180's Value |
|---|---|---|---|
| 28 | 0.6731 | 0.7123 | 0.7834 |
| 52 | 0.0105 | 0.0160 | 0.0146 |
| 27 | 0.6877 | 0.7148 | 0.7373 |

Weighted distance between sample 180 and the average class profiles for each of the two classes is calculated using formula (18):
Distance from class1 profile: 0.0744.
Distance from Class2 profile: 0.0330.

The above distances show that sample 180 is closer to class 2 (a smaller distance) and this is what was predicted above when the output was calculated as 1.64.

Example 2

Personalised Modeling for the Evaluation (Prediction) of Renal Function

In another implementation the method can be used for the evaluation of the level of function of a biological system or an organ of an individual, such as the functioning of the heart, the kidney, etc. This is illustrated here on a case study problem of renal function evaluation based on Glomerular Filtration Rate (GFR) as an accurate renal indicator.

Several nonlinear formulas have been used in practice as "golden standard" global models. The Gates formula (Gates, 1985) uses three variables: age, gender, and serum creatinine, while the MDRD formula (Levey, 1995) uses six variables: age, sex, race, serum creatinine, serum albumin and blood urea nitrogen concentrations. While the existing formulas predict the GFR for patients from different geographic areas with different accuracy, there is no systematic way to adapt these formulas to new data and to personalize the prediction. The method suggested in (Marshal et al, 2005) is closest to this goal, but does not take into account local weighting of the variables. The problem is of prediction/identification as the output values are GFR continuous values.

Here the proposed in the invention method for personalized modeling is demonstrated on the data from (Marshal et al, 2005). In FIGS. 4a-h a new sample x is denoted by a triangle and its nearest neighbours Dx—as circles. All other data from a data set of 584 data samples are shown as "+" sign.

For a chosen sample x (denoted as a diamond) only V=3 variables are used (Element a). A single value for nearest neighbors Kx=30 is used (Element b). Starting with equal weighting of the three variables, different neighborhood sets Dx are selected (Element c) depending on different weights Wx calculated (Element d).

A WWKNN model Mx is created and its local accuracy Ax is evaluated on the 30 samples in Dx (Element e) using formulas (8-11). In FIGS. 4a-h the average local error (formulas 9 and 10) is calculated and visualised accordingly at 8 consecutive iterations of: neighbourhood selection (Element c); variable weighting (Element d) and model creation (Element e). At consecutive iterations different neighborhood areas Dx to the sample x are selected based on the previous local variable weighting Wx. Improved local accuracy Ax of the model Mx may be achieved through these iterations. In the FIGS. 4a-h the local error in the neighbourhood is shown as darkness of the filled neighboring samples (the lighter the color, the less the error).

Figure 4A:
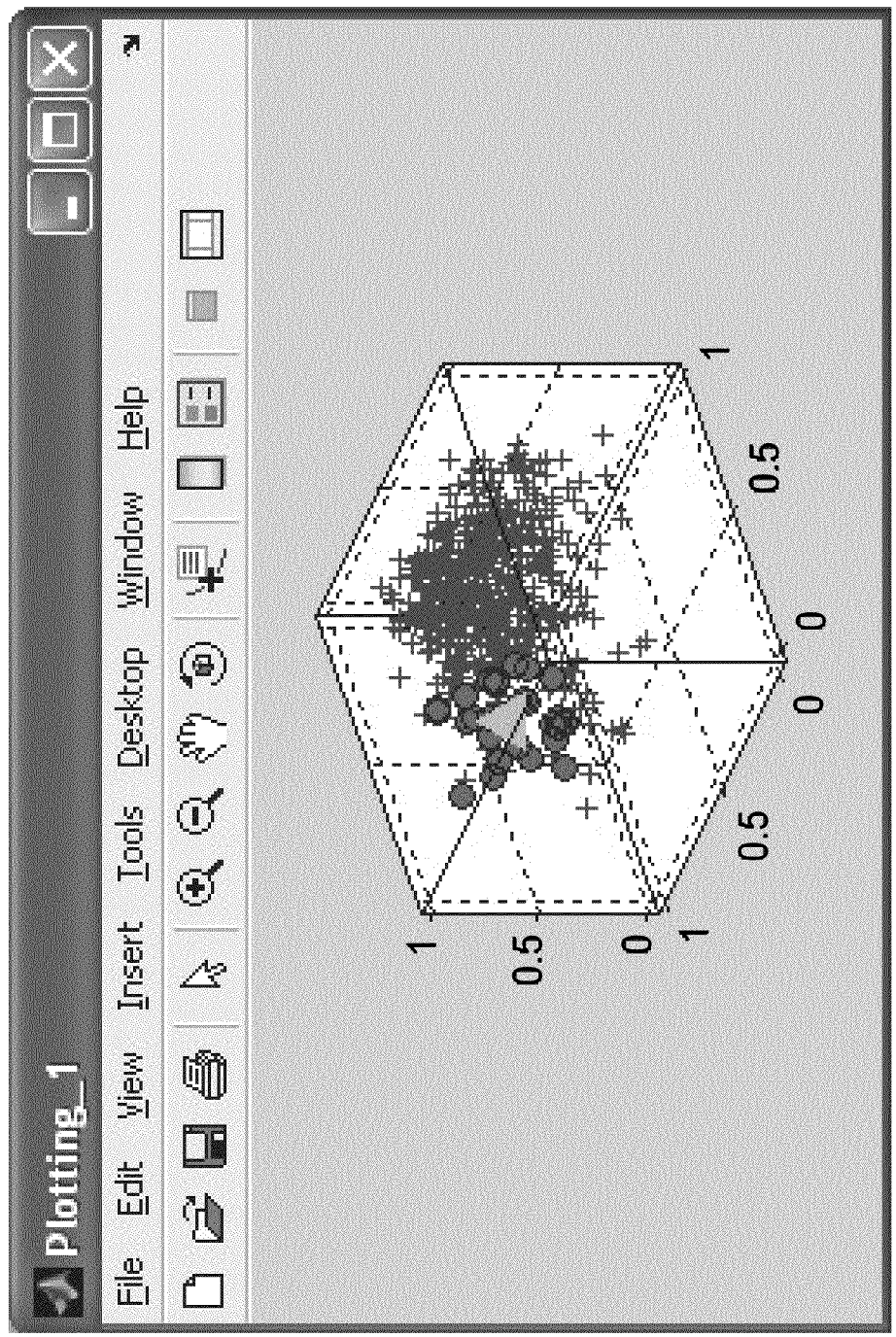
FIG. 4*a-h* Personalized modeling demonstrated in Example 3 on renal function evaluation data (Marshal et al, 2005). A new sample x is denoted by a green triangle and its nearest neighbours Dx—as circles. All other data from a data set of 584 data samples are shown as "+" sign. Vx=3; Kx=30. Staring with equal weighting of the three variables, at 8 iterations shown in (a) to (h) different neighborhood sets Dx are selected depending on different weights Wx calculated. A WWKNN model Mx is created and its local accuracy Ax is evaluated on the 30 samples in Dx. The average local error is calculated and visualized as darkness of the filled neighboring samples (the lighter the color, the less the error).
Figure 4B:
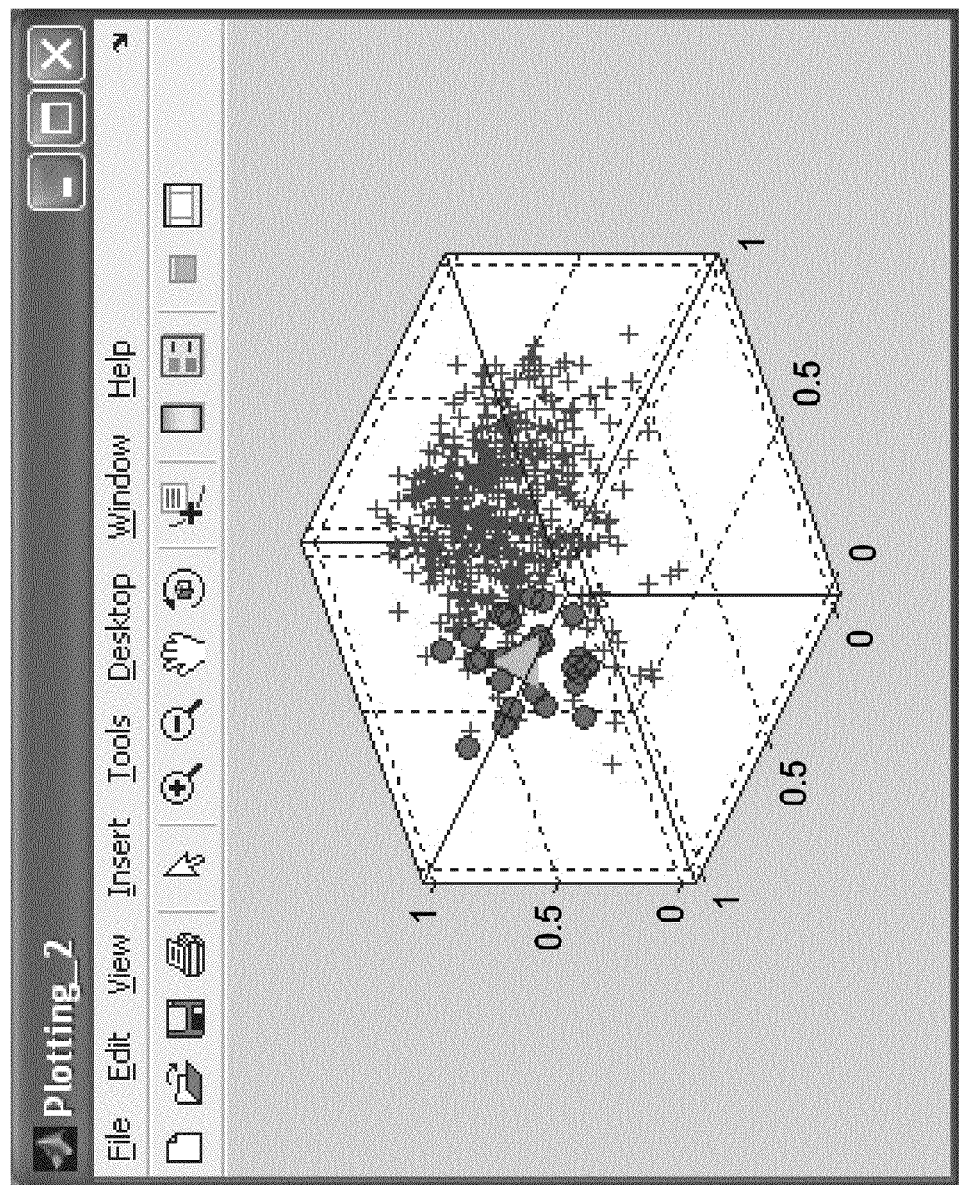
Figure 4C:
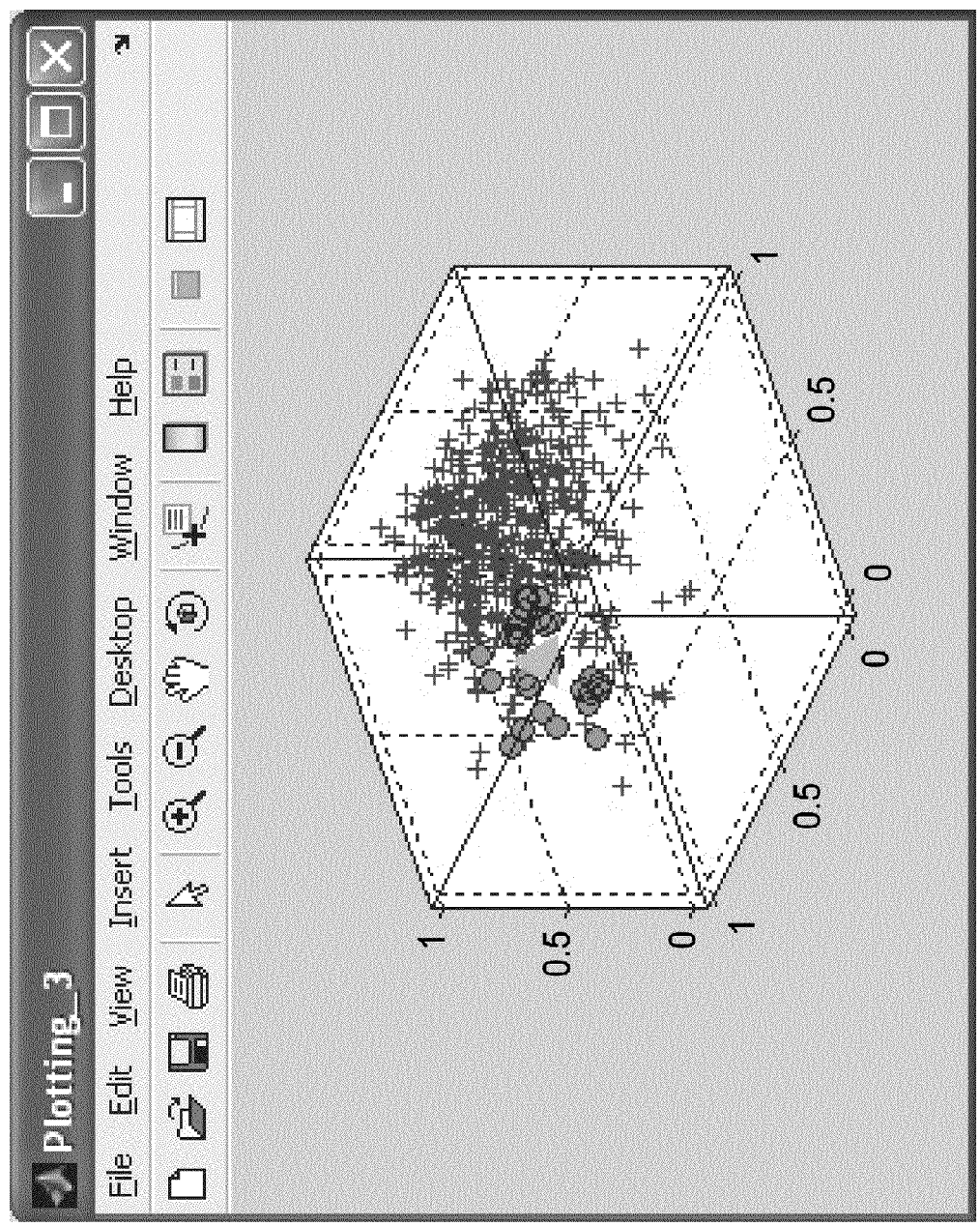
Figure 4D:
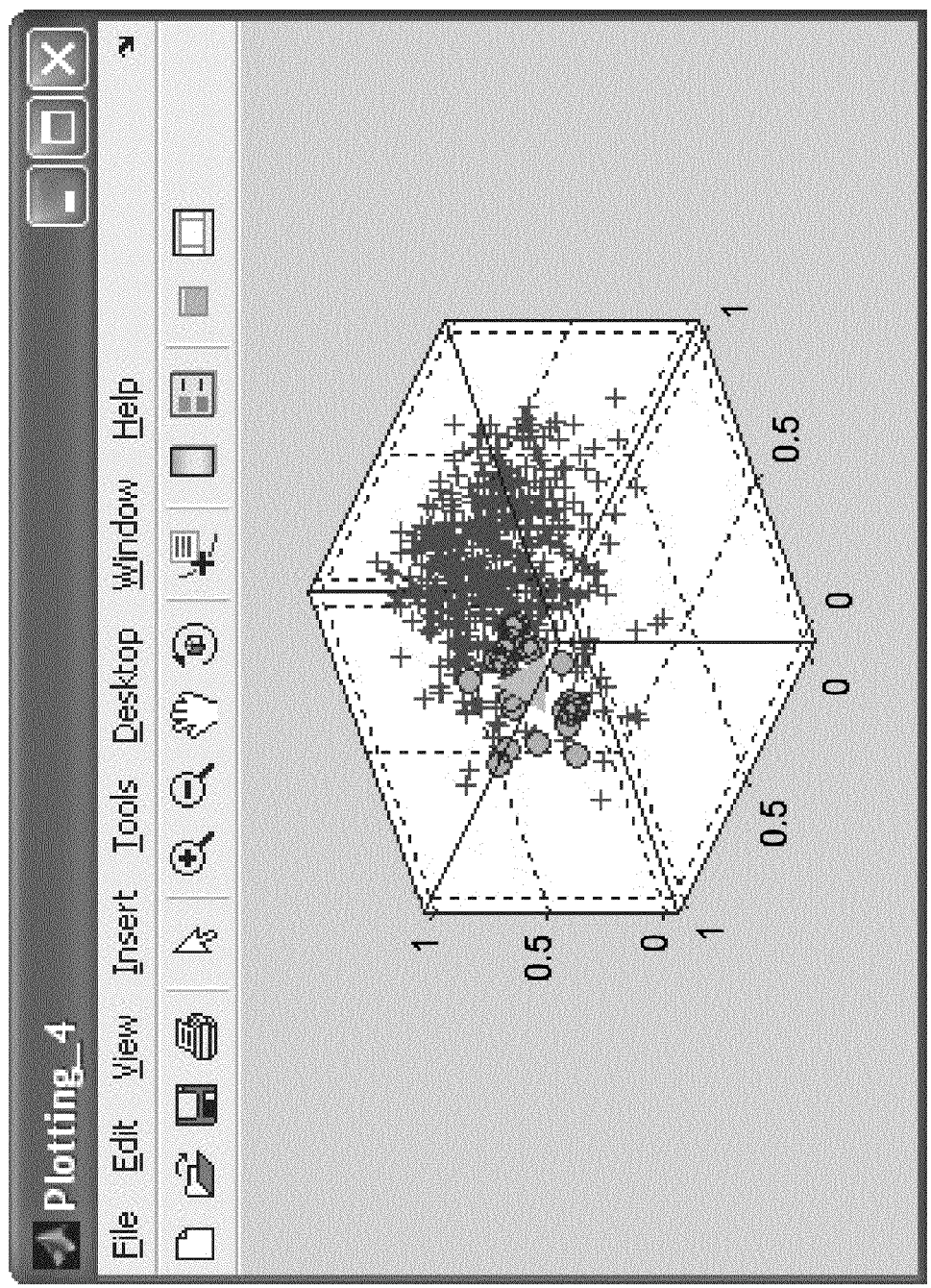
Figure 4E:
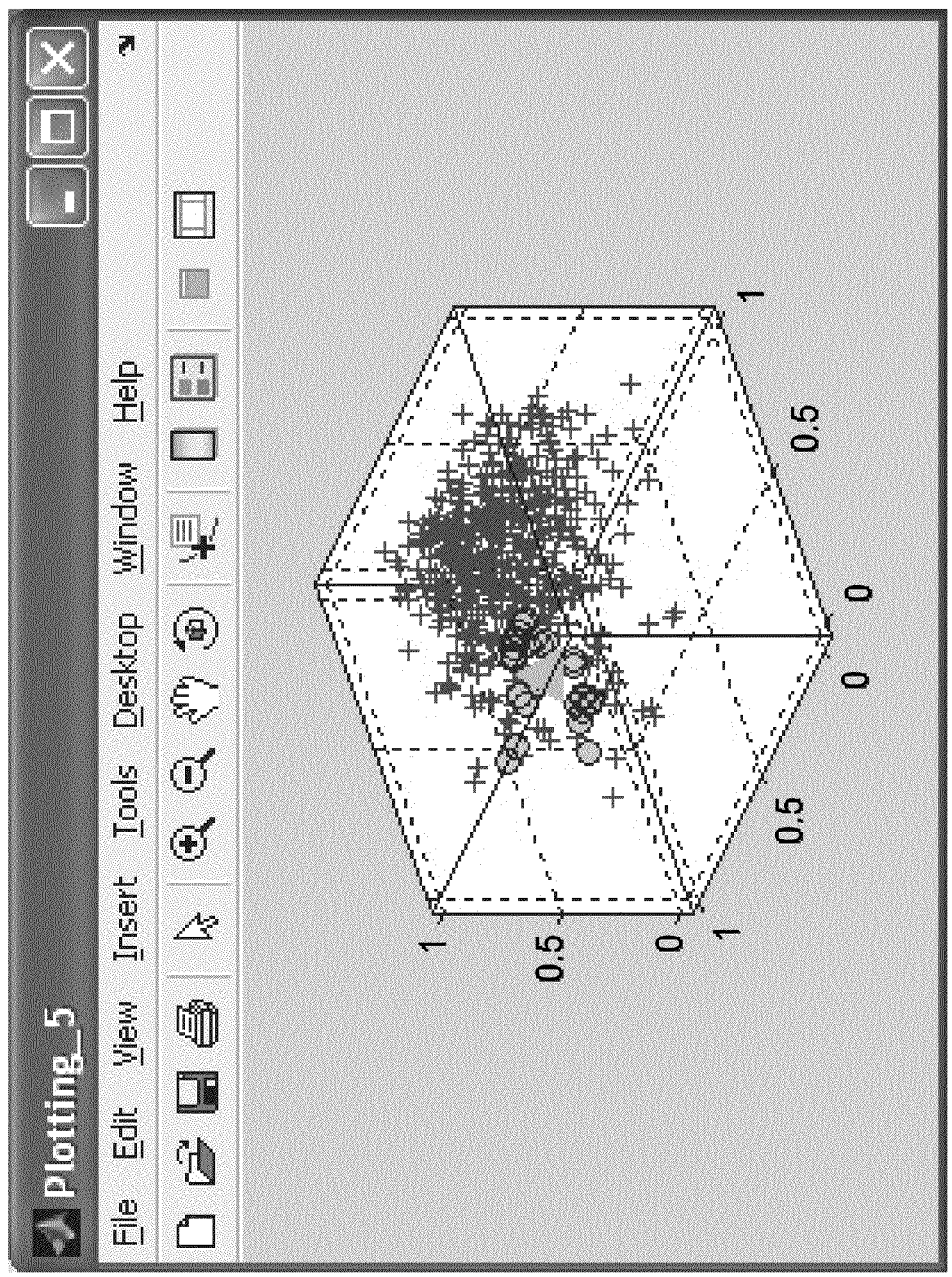
Figure 4F:
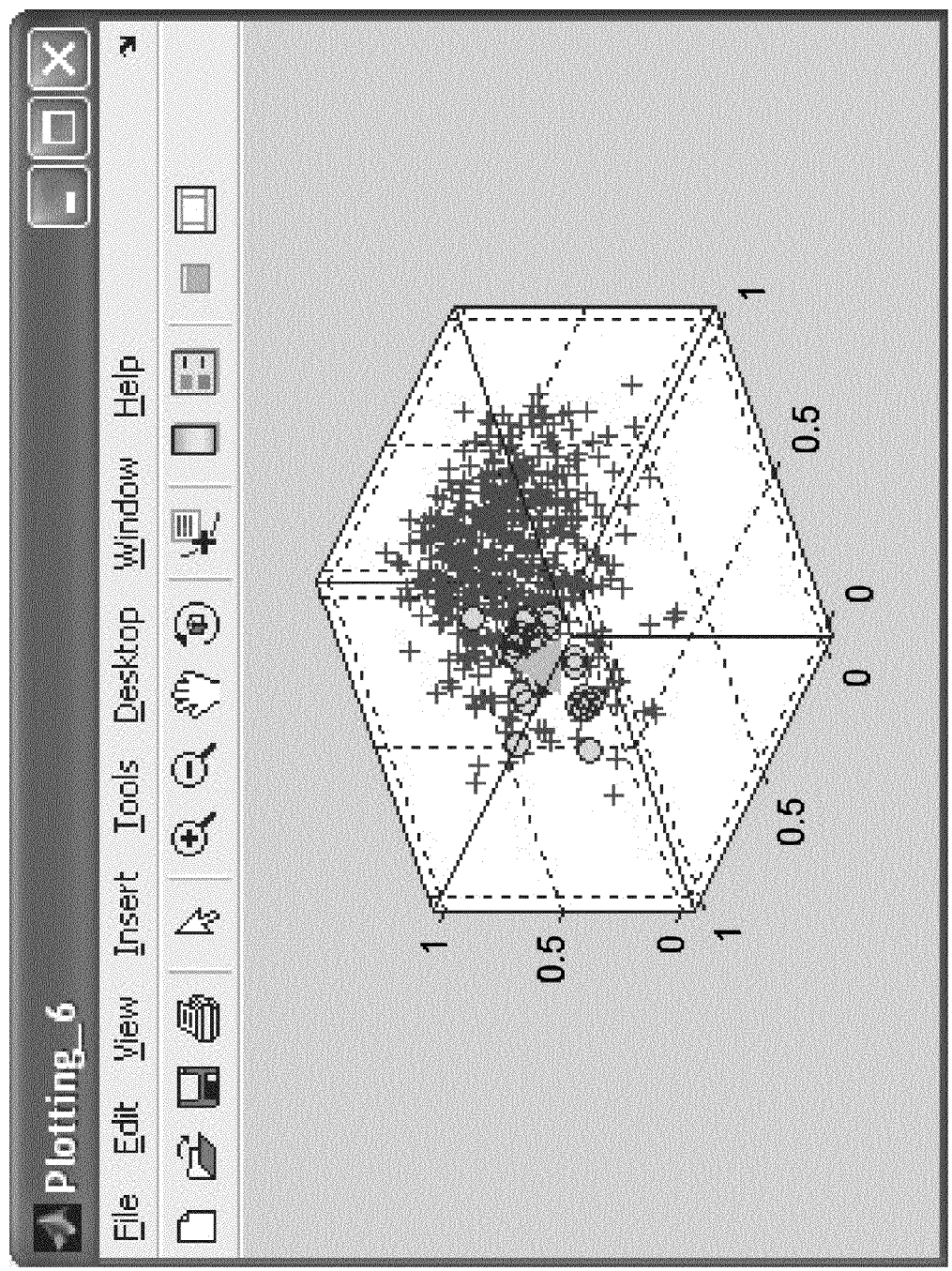
Figure 4G:
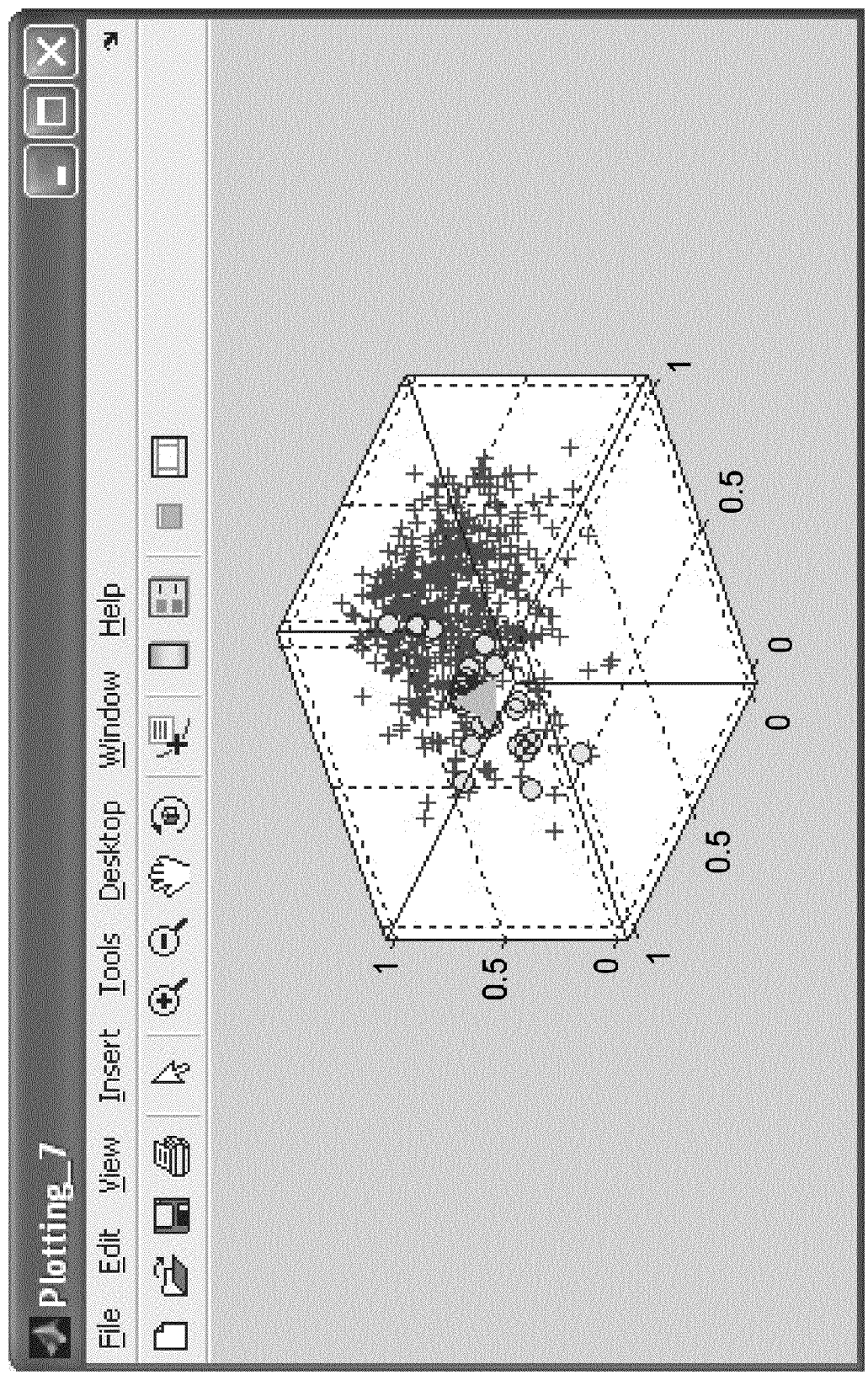
Figure 4H:
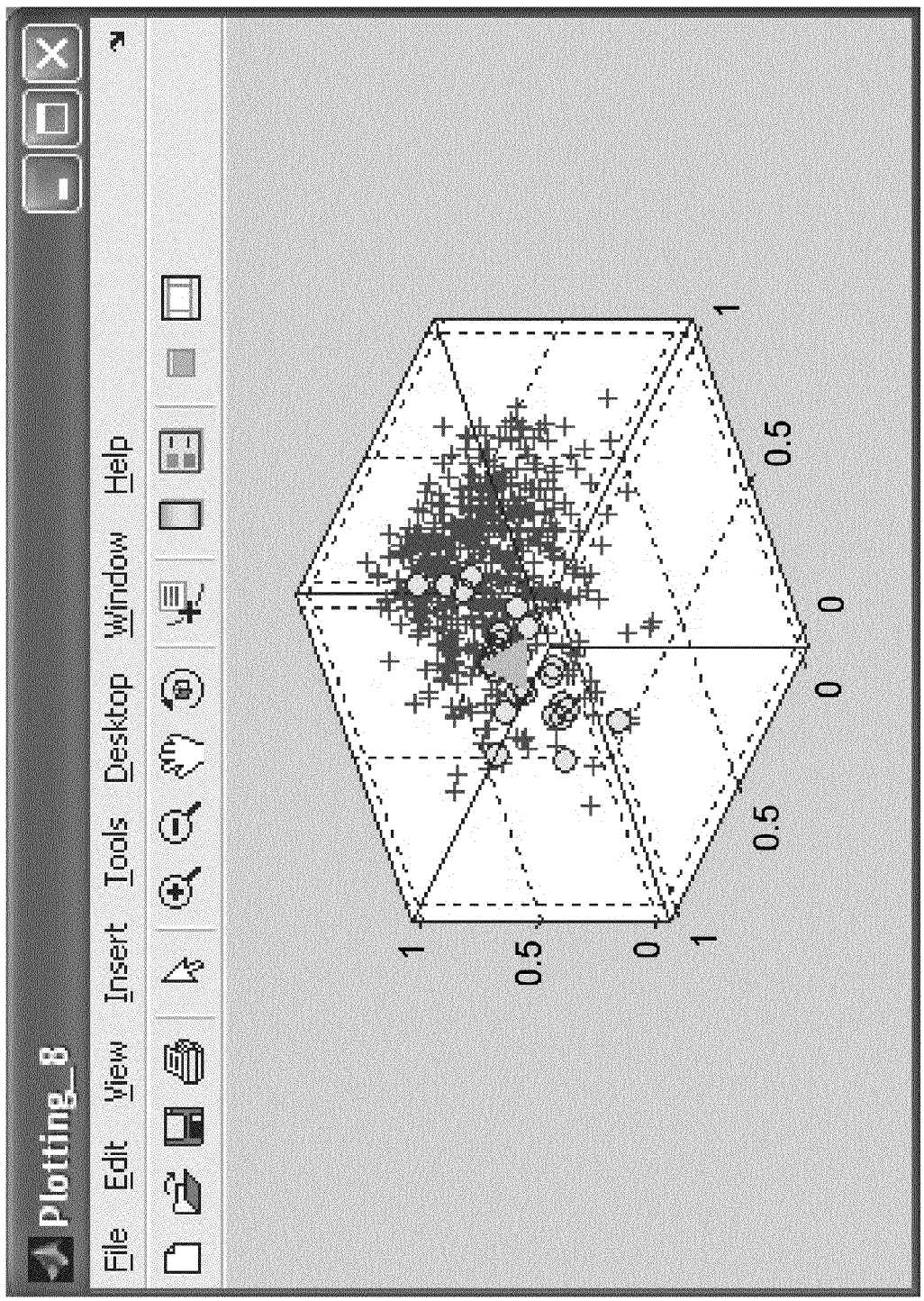

The experiment here demonstrates that the proposed iterative nearest neighbor Dx selection based on iterative local variable weighting Wx leads to an improved result for an individual sample—the Root Mean Square Error (RMSE) may be reduced more than twice (from 15.23 to 6.5) as shown below:

| | Variable | | |
|---|---|---|---|
| | V1 (Age) | V2 (Screa) | V3 (Surea) |
| | Sample x variable values: | | |
| | 0.1250 | 0.5881 | 0.8571 |
| | Variable weights Wx: | | |
| | w1 | w2 | w3 | Local error (RMSE) |
| FIG. 4a (Initial model) | 1.0 | 1.0 | 1.0 | 15.23 |
| FIG. 4h (final model) | 0.1 | 0.8 | 0.1 | 6.5 |

The above profile shows that variable V3 (urea) can be the most important variable for the neighbourhood of the input sample x, followed by variable V2 (Serum creatinine). Using the calculated importance through an exhaustive search procedure leads to an improved prediction (a lower error of 6.5) in the neighbourhood of x. In the initial model, all 3 variables were assumed to have the same importance of 1 and the local error was more than 2 times higher (15.23).

Example 3

Personalised Modeling for Longevity Prediction of Dialysis Patients

In another implementation, the described technology can be used to predict the longevity of a person, based on available data on the longevity of other individuals under similar conditions.

This is illustrated on a case study example of longevity prediction after haemodialysis using the well established DOPPS data as explained below.

A medical dataset is used here for experimental analysis. Data originates from the Dialysis Outcomes and Practice Patterns Study (DOPPS, www.dopps.org)—see also: D. A. Goodkin, D. L. Mapes & P. J. Held, "The dialysis outcomes and practice patterns study (DOPPS): how can we improve the care of hemodialysis patients?" Seminars in Dialysis, Vol. 14, pp. 157-159, 2001.

The DOPPS is based upon the prospective collection of observational longitudinal data from a stratified random sample of haemodialysis patients from the United States, 8 European countries (United Kingdom, France, Germany, Italy, Spain, Belgium, Netherlands, and Sweden), Japan, Australia and New Zealand. There have been two phases of data collection since 1996, and a third phase is currently just beginning. To date, 27,880 incident and prevalent patients (approximately 33% and 66% respectively) have been enrolled in the study, which represents approximately 75% of the world's haemodialysis patients. In this study, prevalent patients are defined as those patients who had received maintenance hemodialysis prior to the study period, while incident patients are those who had not previously received maintenance haemodialysis.

The research plan of the DOPPS is to assess the relationship between haemodialysis treatment practices and patient outcomes. Detailed practice pattern data, demographics, cause of end-stage renal disease, medical and psychosocial history, and laboratory data are collected at enrollment and at regular intervals during the study period. Patient outcomes studied include mortality, frequency of hospitalisation, vascular access, and quality of life. The DOPPS aims to measure how a given practice changes patient outcomes, and also determine whether there may be any relationship amongst these outcomes, for the eventual purpose of improving treatments and survival of patients on haemodialysis.

The dataset for the case study here contains 6100 samples from the DOPPS phase 1 in the United States, collected from 1996-1999. Each record includes 24 patient- and treatment related variables (features): demographics (age, sex, race), psychosocial characteristics (mobility, summary physical and mental component scores (sMCS, sPCS) using the Kidney Disease Quality of Life (KD-QOL®) Instrument), co-morbid medical conditions (diabetes, angina, myocardial infarction, congestive heart failure, left ventricular hypertrophy, peripheral vascular disease, cerebrovascular disease, hypertension, body mass index), laboratory results (serum creatinine, calcium, phosphate, albumin, hemoglobin), haemodialysis treatment parameters (Kt/V, haemodialysis angioaccess type, haemodialyser flux), and vintage (years on haemodialysis at the commencement of the DOPPS). The output is survival at 2.5 years from study enrollment (yes or no).

Several global-, local and transductive modeling techniques have been applied to the DOPPS data to create an accurate classification system. Unfortunately the best models published so far achieve only 74% accurate prediction (for a comparative analysis of different methods, see: Ma, Q Song, M. R. Marshall, N Kasabov, TWNFC-Transductive Neural-Fuzzy Classifier with Weighted Data Normalization and Its Application in Medicine. CIMCA 2005, Austria The application of the method of the described technology leads to a significant improvement of the accuracy and to a personalised model derived that can be used to design a specific treatment for a person.

In relation to the experiment below (to test the method of the present invention) the number of training samples is 958 and initial number of features V=24. The classification method, to be utilized by the method of the described technology is WWKNN with a fixed classification threshold of 0.5.

The number of neighbouring samples is Kx=50. Sample #5 is taken as a new sample for which a personlised model is developed and tested giving 84% local accuracy of prediction.

After several iterations according to the proposed method, the following best parameters and model are obtained:
Vx=2 (features 3 and 13);
SNR normalised weights Wx (formulas 8 and 5):
  feature 3: 0.5254;
  feature 13: 0.4746
Kx=50;
Dx=(455 405 300 107 451 576 78 895 589 612 77 725 207 705 44 529 160 605 444 869 43 48 348 83 331 356 846 238 97 278 882 894 484 79 447 68 526 42 525 179 50 415 718 195 210 240 298 118 766 664 180 121 410 411 108 786 81 788 499 787 672 631 905 872 407 886 881 237 62 889 239 586 206 396 915 952 320 891 867 104 722 393 35 893 443 523 857 34 771 476 372 865 609 52 26 395 658 38 687 151 851 126 432 798 321 712 453 618 211).
An WWKNN model is created. Best local accuracy on training data, calculated using formulas (9-10), is 84.40%.

The output y of sample #5 is calculated using formula (II):

| sample | output | actual class | predicted class |
|---|---|---|---|
| 5 | 1.99 | 2 | 2 |

Personalised profiling is performed for sample #5 (Element i) from the invention using formula (16):

| Feature | Mean Value(Cls1) | Mean Value(Cls2) | Sample 5's Value |
|---|---|---|---|
| 3 | 0.5161 | 0.5529 | 0.0000 |
| 13 | 0.4332 | 0.4557 | 0.5000 |

Weighted distance between sample 5 and the average class profile is calculated using formula (18):

| Cls1 | Cls2 |
|---|---|
| 0.3029 | 0.3115 |

An improvement scenario (Element j) is designed via elements (I)-(III) of the described technology using formulas (19) to (21):

The sample x (sample 5 from the data base), for which a personalised model is created, is predicted to be of class 2 (bad outcome). A possible scenario for the person to become of class 1 (good outcome) may be designed based on the changes in the two selected variables (3 and 13) for the current person's values to the average values of the persons in the neighbourhood Dx of x who belong to class 1 (the good outcome):

| Variable | Person 5 values | Average_class_1_values | Desired_changes | Importance |
|---|---|---|---|---|
| 3 | 0.0000 | 0.5161 | 0.5161 | 0.5254 |
| 13 | 0.5000 | 0.4332 | −0.0668 | 0.4746 |

Example 4

Feature Selection and Personalised Modeling for Disease Outcome Prediction Based on Gene Expression and Other Data In one implementation, the proposed method and system may be applied for predicting the outcome of a disease, such as cancer, based on gene expression, protein and/or clinical data.

To illustrate this claim we use a case study problem and a publicly available data set from Bioinformatics—the DLBCL lymphoma data set for predicting survival outcome over 5 years period. This data set contains 58 vectors—32 cured DLBCL lymphoma disease cases, and 26—fatal (see Shipp, M. A., K. N. Ross, et al. (2002). "Supplementary Information for Diffuse large B-cell lymphoma outcome prediction by gene-expression profiling and supervised machine learning." Nature Medicine 8(1): 68-74. There are 6,430 gene expression variables. Clinical data is also available for 56 of the patients represented as IPI—an International Prognostic Index, which is an integrated number representing overall effect of several clinical variables.

The task is to:
(1) Create a personalised prognostic system that predicts the survival outcome of a new patient x for whom same gene expression variables are available.
(2) To design a personalised profile for x that can be used to provide an explanation for the prognosis and design of treatment;
(3) To find markers (genes) that can be used for the design of new drugs to cure the disease or for an early diagnosis.

This data has been first published in (Shipp et al, 2002) where a leave-one-out un-biased cross validation modeling was performed. For every sample, a set of features was selected from the rest 57 samples using the signal-to-noise ratio, a model was created and tested on this sample with an overall accuracy of 70%. Here, using the same data and the same cross validation un-biased procedure as detailed in (Shipp et al, 2002), but applying the method of the present invention, an overall accuracy close to 90% may be achieved. As an illustration, here a personalized model for sample #34 may be created using: 57 samples from the data set, each of them described as a vector of 6430 variables (genes)

A WWKNN model, with a threshold of 0.5, was derived and a profile of the sample 34 was created along with an improvement scenario as sample #34 was correctly predicted by the created model to belong to the class of the fatal outcome.

After the iterative parameter optimization in Elements a-h) the following model Mx may be created.

Kx=26 neighbours of sample 34;

Neighbouring area Dx=(24 44 39 29 56 31 52 1 20 55 47 49 40 25 17 18 16 57 46 48 23 42 6 3 50 41);

5 features are selected as optimal for sample 34 and weighted through SNR for the area Dx (formulas 8 and 5):

| Feature (gene) | Weighted SNR value |
|---|---|
| 2915 | 0.2182 |
| 3513 | 0.2091 |
| 5460 | 0.1915 |
| 4533 | 0.1910 |
| 5423 | 0.1902 |

Figure 5A:
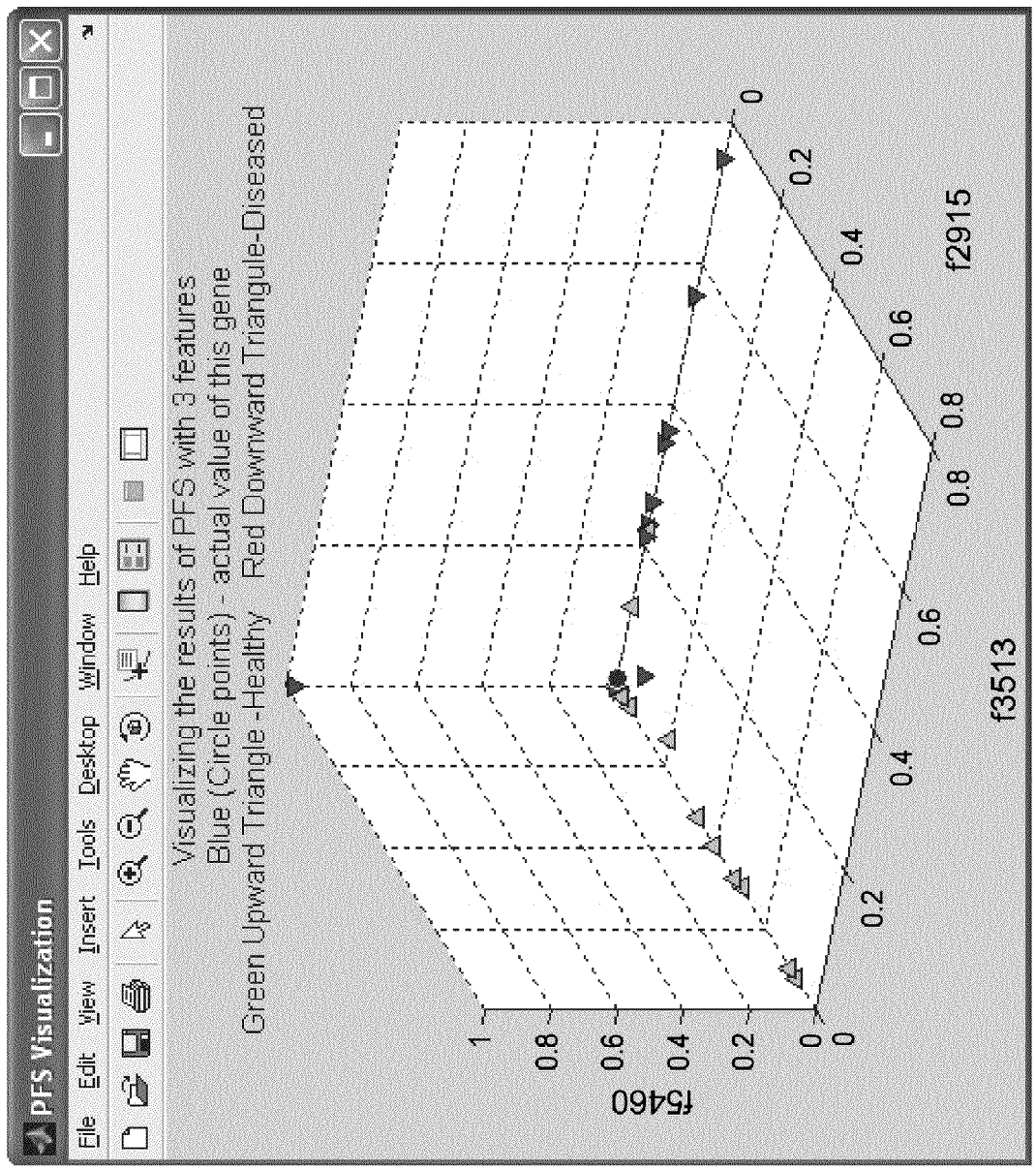
FIG. 5a A sample x from the Lymphoma outcome prediction data set (Shipp et al, 2002) shown with 26 neighboring samples in the 3D space of the top 3 gene expression variables (see Example 4).

FIG. 5a shows the 26 samples from the Dx in the 3D space of the top three variables only (genes #2915, 3513, 5460).

A WWKNN model may be created and tested as per Element e. The best local accuracy Ax in Dx on the 26 data samples, calculated using formulas (9-10) is 80%.

The calculated output for sample 34 using formula (11) is 0.59 and as the classification threshold is 0.5, sample 34 is classified to belong to class 1 (bad outcome, output value 1)).

A profiling of sample 34 is designed using formula (16):
Profiling:

| Feature | Mean Value(Cls0) | Mean Value(Cls1) | Sample 34's Value |
|---|---|---|---|
| 2915 | 166.5706 | 37.4990 | 20.0000 |
| 3513 | 50.9251 | 187.9606 | 201.7022 |
| 5460 | 20.0000 | 35.5601 | 20.0000 |
| 4533 | 198.5793 | 48.7171 | 20.0000 |
| 5423 | 43.7684 | 21.2006 | 20.0000 |

A weighted distance between sample 34 and the average class profiles for Class 0 (good outcome) and Class 1 (fatal outcome) is calculated using formula (18) as:
102.1396 (for class 0)
15.3837 (for class 1).

The above distances show that sample 34 is closer to the average profile of the fatal outcome (class 1) than to the good outcome (class 0) that is also confirmed by the predicted above output value of 0.59 for sample 34.

Figure 5B:
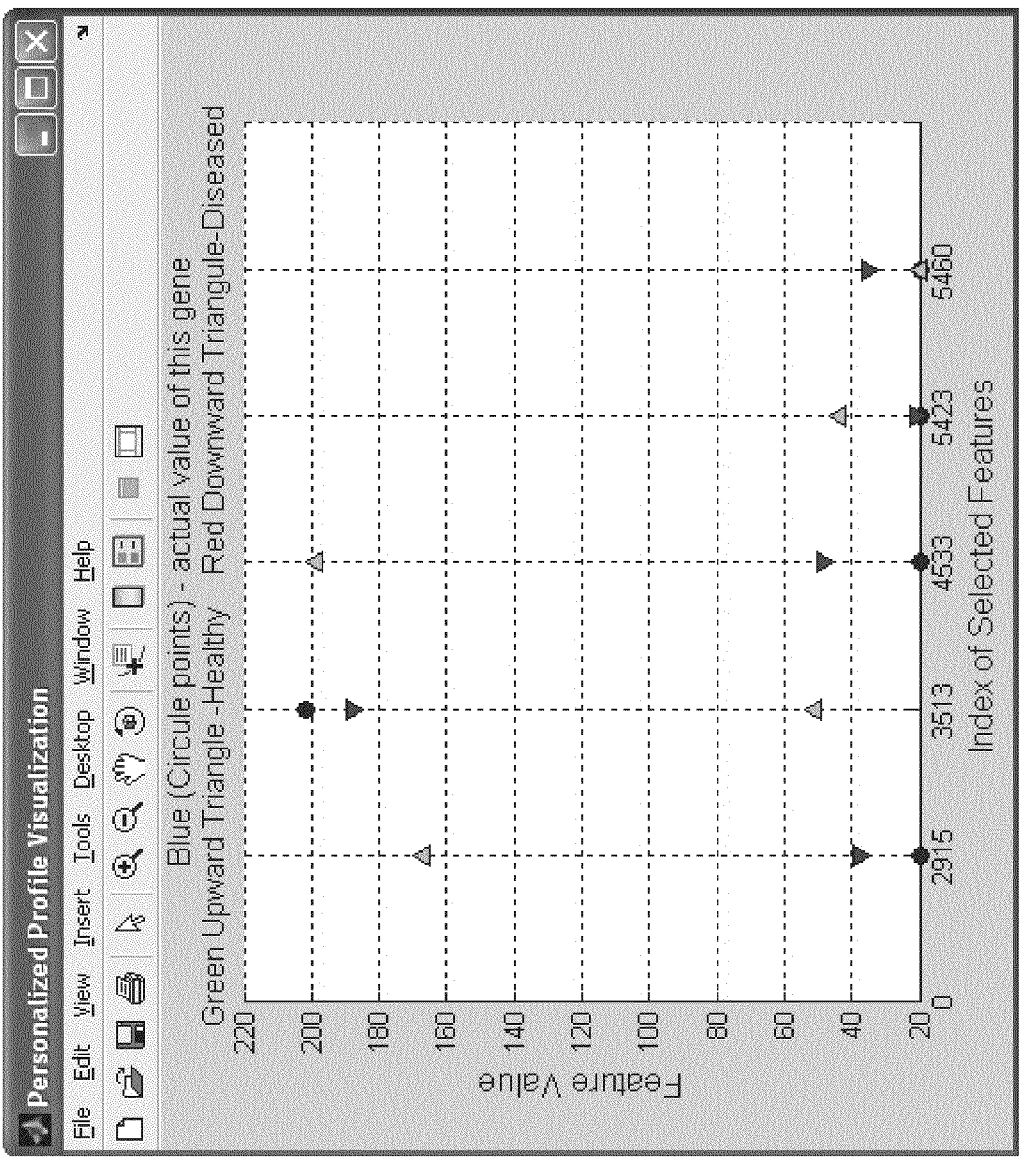
FIG. 5b An improvement scenario for sample x from the Lymphoma outcome prediction data set (Shipp et al, 2002) for which a fatal outcome (class 1) is predicted. The figure shows how much each feature variable (gene expression value) needs to be changed for this person to <<move>> to the average good outcome profile (see Example 4).

A scenario for the improvement of a person 34 in terms of required changes in the gene expression values of each feature variable (gene) according to Element J from the invention (formulas 19-21) is shown below and illustrated in FIG. 5b:

| Gene | Actual_Value | Desired_aver_profile | Desired Improvem. | Importance |
|---|---|---|---|---|
| 2915 | 20.0000 | 166.5706 | 146.5706 | 0.2182 |
| 3513 | 201.7022 | 50.9251 | −150.7771 | 0.2091 |
| 5460 | 20.0000 | 20.0000 | 0.0000 | 0.1915 |
| 4533 | 20.0000 | 198.5793 | 178.5793 | 0.1910 |
| 5423 | 20.0000 | 43.7684 | 23.7684 | 0.1902 |

The above improvement scenario can be interpreted in the following way: In order to improve the outcome for person #34 towards the good outcome (survival), some genes (proteins) need to change their expressions through drug intervention or other means, so that: genes 2915, 4533 and 5423 are stimulated for a higher expression; gene 3513 is suppressed for a lower expression; and gene 5460 is unchanged. This interpretation has the potential to be used for a personalized treatment (e.g. drug) design for this person, where only genes 2915, 4533, 5423 and 3513 are affected by the treatment, also taking into account their importance, defined as a local weight in the neighborhood Dx.

After a certain period of treatment, a new model and a new profile for this person, based on a new input vector x' can be derived, using the same invention, and the previous treatment modified accordingly, until this person is cured.

Aspects of the described technology have been described by way of examples only and it should be appreciated that modifications and additions may be made thereto without departing from the scope of the appended claims.

Example 5

Personalised Modelling for Risk of Disease Evaluation, Diagnosis, Treatment and Drug Design Using DNA SNP Sequence Data An individual DNA sequence, that can be obtained from any cell of a living organism (e.g. human, animal, plant, virus) carries not only the inherited traits or risk of diseases through generations, but also shows the current state of the organism in terms of accumulated mutations during life time. This information can be used to predict the unique personalized trait of the organism, risk of disease or diagnosis, at the time of the DNA sequencing subject to sufficient data samples of measured DNA and their traits. Collecting individual DNA sequence data and measuring Single Nucleotide Polymorphisms (SNP) (eg A to A, A to G, G to G) for an individual and a large population of individuals becomes easy and cheap with the advancement of the microarray technologies.

Such data has been collected and published as part of Genome-wide Association Scan projects (GWAS). Results of 374 such projects for over 100 human traits and diseases are published in (Hindorff L A, Sethupathy P, Junkins H A, Ramos E M, Mehta J P, Collins F S, and Manolio T A. Potential etiologic and functional implications of genome-wide association loci for human diseases and traits. Proc Natl Acad Sci USA, May 27, 2009) and the collected data is available on the Internet. Such GWAS project is also the WTCCC project in the UK, results published in Nature, 2007 (The Welcome Trust Case Control Consortium, Genome-wide association study of 14,000 cases of seven common diseases and 3,000 shared controls, Nature, vol. 447, 2007, 661-670) and obtained data available from the Internet. The publications so far report on the statistically derived population risk of disease (trait) for single SNPs signals (see also: Lea, Rod, Donia Macartney-Coxson, David Hall, Bushra Nasir and Lyn Griffiths, A Novel Bioinformatic Approach for Identifying Genomic Signatures of Disease Risk, ESR Ltd Report, Porirua, New Zealand, 2009). The challenge is to use the available SNP data to derive a personalized risk and SNP (gene) signature for a new individual, along with possible treatment and drug design, that take into account the specific interaction and combination of several SNPs specific for this person.

We claim that the proposed in the patent specification method is applicable to SNP data (e.g. wtccc.org) to obtain an individual SNP signature for every new person and predict the individual risk of this person for the following diseases included in the UK WTCCC study, as illustrated later in this Example:
  Bipolar disorder;
  Coronary artery disease;
  Crohn's disease;
  Hypertension;
  Rheumatoid arthritis
  Type 1 Diabetes;
  Type 2 Diabetes;
  Tuberculosis;
  Breast cancer;
  Multiple sclerosis;
  Ankylosing spondylitis;
  Autoimmune thyroid disease
as well as to predict the individual risk or diagnosis for other diseases based on data collected and published elsewhere including brain injury and brain degenerative diseases, such as:
  Stroke;
  Alzheimer disease;
  Mental retardation;
  Schizophrenia
  and many more

Here we describe how the proposed methodology can be applied to SNP data, exemplified on the WTCCC data for any of the diseases above. We take as a concrete example the Crohn's disease.

First, based on the SNPs data of diseased and control persons, unique SNPs for the diseased when compared to the controls are statistically identified using the method from (Nature, 2007)). An example of identified 9 SNP association signals for the Crohn's disease in the WTCCC project, across all chromosomes, is given in FIG. 6. Each SNP association signal (area from the DNA) may contain several SNPs and is part of a gene that could be a possible target for a treatment or drug design.

Figure 7:
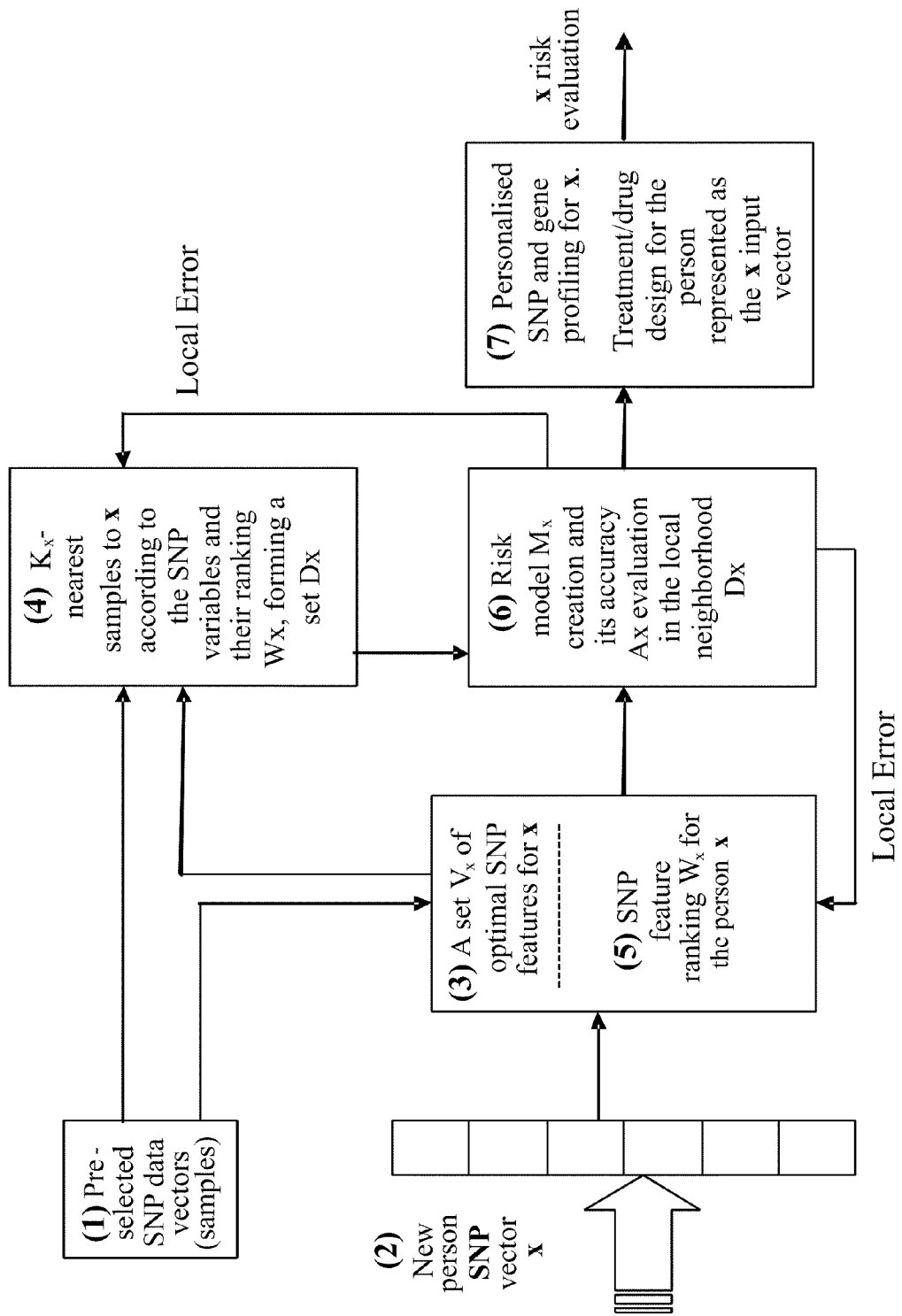
FIG. 7 A block diagram of a personalised modelling, profiling and risk analysis system for SNPs DNA data sequence analysis, obtained as an application system from the general block diagram in FIG. 1 (see Example 5).
Figure 8:
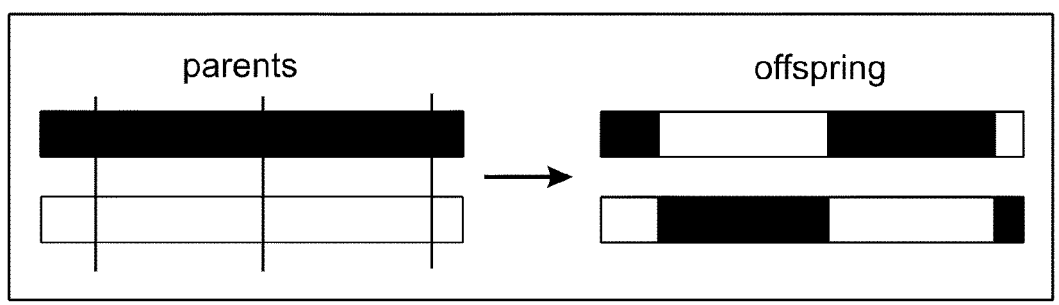
FIG. 8 shows a three point cross over operation, where the two individual cross over through exchanging their genes in 4 sections, based on usually randomly selected 3 points.

The methodology of the described technology may applied here on a data set D of samples (both controls and diseased) that contain selected SNPs to create a personalized model for a new person, represented as input vector x containing the same SNPs, for the prognosis of the risk of this person of the disease (or a trait under consideration) and to create a SNP and gene signature of the person for a possible treatment or a drug design. The following elements are realized iteratively (as also shown in the block diagram of FIG. 7 which is derived from the general block diagram in FIG. 1).

According to another aspect of the described technology method of creating an optimised personalized model of a person's medical condition based on an analysis of selected SNPs is provided comprising:
  (a) determining a number of SNP variables and selecting a subset of SNPs variables Vx from a dataset D;
  (b) determining a number Kx of nearest neighbors of SNP vectors to x from D;
  (c) selecting a subset Dx from the set D of Kx neighboring samples to x according to the set of SNP variables Vx;
  (d) ranking the SNP variables from Vx according to their discriminative power in Dx, e.g. to discriminate controls versus diseased in Dx;
  (e) creating a personalised prognostic model Mx for the risk of disease of person x (e.g. a linear regression, a neural network or else) with parameters Px, using the selected variables Vx and nearest samples in Dx.
  (f) testing the predicted by Mx risk for every sample from Dx and compare it to the known risk calculating the average local error Ax across all samples from Dx.
  (g) storing all parameters and values from the above elements (a) to (f) as results of the current iteration.
  (h) repeating elements (a) to (g) until the best local accuracy is achieved.

Figure 6:
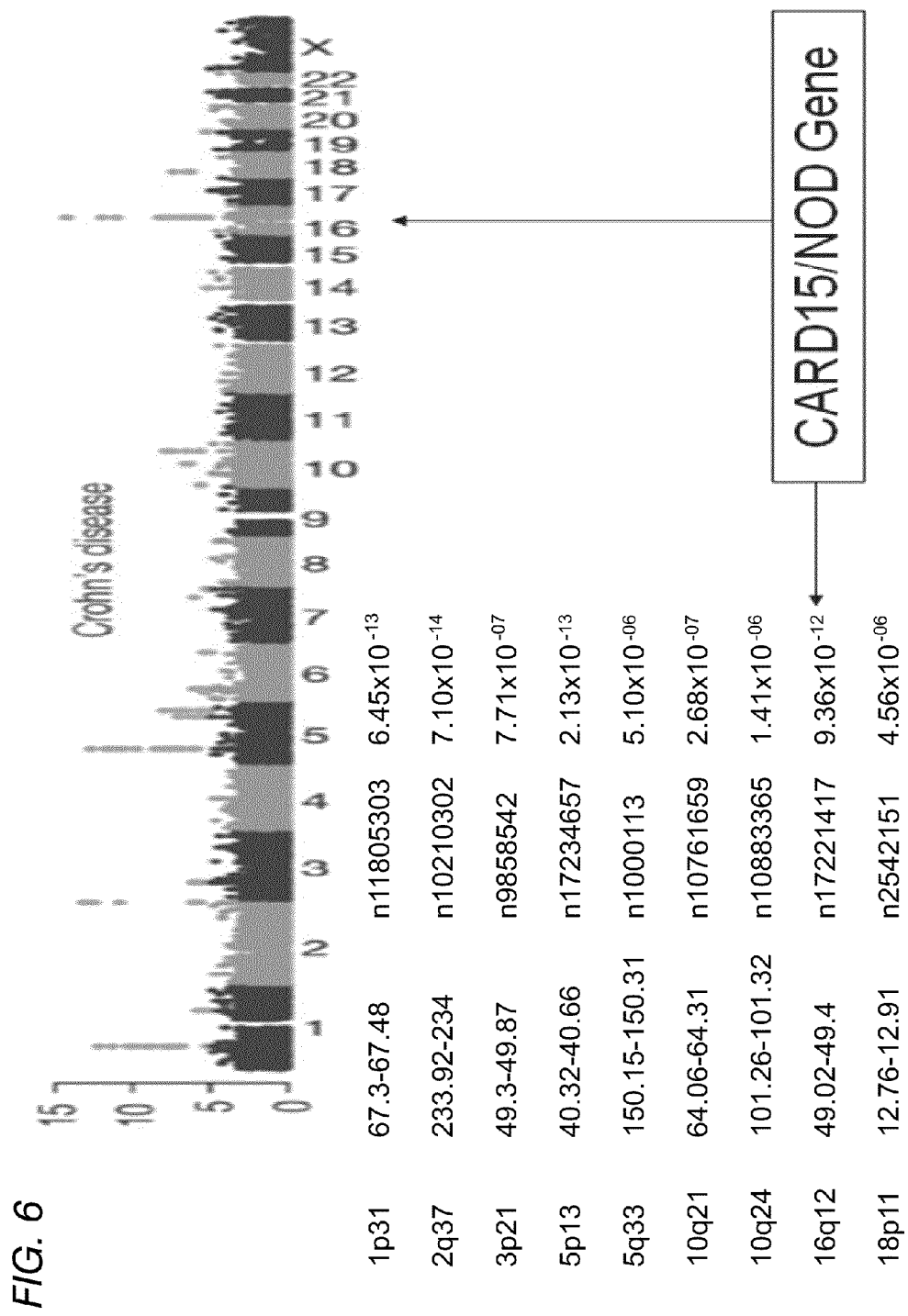
FIG. 6 Identified SNP regions (associated signals) for the Crohn's disease Example 5) and their mapping on the chromosomes. One gene, related to a SNP region, is identified that may be used as a treatment or drug target (modified from R. Lea at al, 2009).

According to another aspect of the described technology a method of calculating the risk of disease from an optimized SNP model of a subject derived substantially as described above is provided, the method comprising:
  (i) using the model Mx derived from the above iterations to calculate the risk y for the sample x.
  (ii) creating a SNP profile of x and the corresponding gene profile by mapping the SNPs from the final set Vx into genes as illustrated in FIG. 6.
  (iii) creating a scenario for treatment/drug design that includes a set of SNPs/genes and the needed changes for the person x to match in the future the average profile of the control samples from Dx.

The data sub-sets and parameters Vx, Wx, Kx, Dx, Mx, Px are selected and optimised together through several iterations of the procedure above as described in the method, so that the best accuracy of the personalised prognosis, or close to it is achieved as a target/objective function. The method allows for a dynamic adaptation, monitoring and improvement of the personalised model should new data about the person or the population become available over a time period. For example, in some years time aging and environmental factors (radiation, nutrition, smoking, drugs, etc) might have made impact on the person's DNA and new risk evaluation would be needed when possibly new known samples will be added to the data set D.

To illustrate the use of the proposed methodology on SNP data for disease risk prognosis, we will use a subset of 1048 samples from the WTCCC data repository related to both control subjects (488, no disease) and Crohn's diseased subjects (560) for which already 53 SNPs are identified as statistically significant for the whole population at a pre-processing stage. The data was kindly provided by Dr Rod Lea from the Environmental Science Research Ltd, CRI, New Zealand.

We will show here the development of a personalised model for the prediction of Crohn's disease of a new subject (input vector x).

After several iterations of a genetic algorithm (GA) optimisation procedure to optimise together features, number of nearest samples and model parameters, the following results were obtained as the best results for the sample x:

(a) The number of SNPs Vx that best predicts the outcome for x is 10 and the SNP features are the following ones (out of 53): 40, 10, 19, 42, 21, 34, 45, 49, 30, 22.

(b) The optimal number Kx of nearest samples is 67 (out of 1048 total number of samples).

(c) The nearest samples selected are #: 647 742 458 255 258 513 697 245 486 728 823 920 1035 24 140 144 394 581 612 710 775 907 910 916 1027 131 273 336 585 635 646 672 699 763 812 816 819 849 958 1013 56 165 210 226 246 266 272 557 575 576 671 724 735 752 754 770 800 871 884 934 952 966 981 1032 44 52 61

(d) A weight vector for the Vx variables is obtained.

(e) A WKNN model is used for classification with an optimised parameter—a class decision threshold of 0.19.

(f) The local accuracy is evaluated as 85% correct.

(g) The WKNN model is used to calculate the output risk for x as y=0.57. As this sample was with a known outcome to be 1 (diseased) the peronsalised model correctly predicted this outcome (using an optimised threshold of 0.19).

(h) A personalised SNP signature for x is developed based on the 22 control samples in the neighbourhood of 97 samples and 45 diseased. The local probability of each of the three SNPs denoted as 0, 1 and 2 in each of the controls and diseased samples of the neighbourhood of x are the following:

| SNP ID | Control (22) | | | Diseased (45) | | | Actual Value of the SNP in x |
|---|---|---|---|---|---|---|---|
| | 0 | 1 | 2 | 0 | 1 | 2 | |
| 40 | 0.55 | 0.45 | 0.00 | 0.38 | 0.58 | 0.04 | 1 |
| 10 | 0.64 | 0.36 | 0.00 | 0.76 | 0.24 | 0.00 | 0 |
| 19 | 0.77 | 0.23 | 0.00 | 0.67 | 0.22 | 0.11 | 0 |
| 42 | 0.73 | 0.18 | 0.09 | 0.71 | 0.24 | 0.04 | 0 |
| 21 | 0.36 | 0.50 | 0.14 | 0.31 | 0.58 | 0.11 | 1 |
| 34 | 0.64 | 0.36 | 0.00 | 0.80 | 0.20 | 0.00 | 0 |
| 45 | 0.32 | 0.68 | 0.00 | 0.36 | 0.51 | 0.13 | 1 |
| 49 | 0.59 | 0.41 | 0.00 | 0.58 | 0.42 | 0.00 | 1 |
| 30 | 0.09 | 0.50 | 0.41 | 0.16 | 0.80 | 0.24 | 2 |
| 22 | 0.50 | 0.50 | 0.00 | 0.56 | 0.44 | 0.00 | 0 |

It is seen from the above table that SNP features #40, 10 and 34 are prominent in the diseased group versus the control group in the neighbourhood of x. These SNPs may be mapped into genes and then explored as possible drug or treatment targets.

Aspects of the described technology have been described by way of example only and it should be appreciated that modifications and additions may be made thereto without departing from the scope thereof.

REFERENCES

General References and Citations (1) Personalized medicine journal. Available at the "future-medicine" web site.
(2) David S Resnick†, Ronald I Eisenstein, J Amelia Feulner & Leena H Karttunen, Creating and enforcing patent rights in the fast moving field of personalized medicine, February 2006, Vol. 3, No. 1, Pages 89-94, (doi: 10.2217/17410541.3.1.89)
(3) Personalized Medicine Coalition. Available at the Personalized Medicine Coalition web site.

PMC membership encompasses a broad spectrum of academic, industrial, patient and healthcare provider constituencies. Membership is open, but not limited, to universities and academic medical centers, non-profit research entities, relevant trade associations, patient advocacy groups, government officials (ex-officio), healthcare organizations, healthcare providers, payers, information technology companies and research-based commercial companies that offer an array of products and services including research tools, diagnostic technologies and products, screening services and therapeutic interventions.

(4) ProQuest database: *The Economics of Personalized Medicine: A Model of Incentives for Value Creation and Capture*
(5) Louis P Garrison Jr, M J Finley Austin. *Drug Information Journal*. Ambler: 2007. Vol. 41, Iss. 4; pg. 501, 9 pgs, Personalized medicine is a concept promoted as a new paradigm for health care delivery, with particular emphasis on more tightly linking genomics-based diagnostics and therapeutics. Previous analyses focused on the pharmaceutical market; this analysis also addresses the incentives to develop linked genomics-based diagnostics and the broader public policy implications. Using a standard economic framework of an insurer-payer negotiating reimbursement with manufacturers of an innovative, targeted diagnostic and a companion patented therapeutic, several illustrative hypothetical scenarios are developed. The relative importance of the key economic factors is examined, including whether the reimbursement system is value or cost based, whether the therapeutic is already marketed, the strength of diagnostic intellectual property, and a current year versus longer time frame. The results suggest that health systems reforms that promote value-based, flexible reimbursement for innovative, patent-protected diagnostic and therapeutic products are critical to create stronger economic incentives for the development of personalized medicine.

(6) A call for the creation of personalized medicine databases. Author: Gurwitz, David[1] Lunshof, Jeantine E.[2] Altman, Russ B.[3]

Source: *Nature Reviews Drug Discovery*; January 2006, Vol. 5 Issue 1, p 23-26, 4p Abstract: The success of the Human Genome Project raised expectations that the knowledge gained would lead to improved insight into human health and disease, identification of new drug targets and, eventually, a breakthrough in healthcare management. However, the realization of these expectations has been hampered by the lack of essential data on genotype-drug-response phenotype associations. We therefore propose a follow-up to the Human Genome Project: forming global consortia devoted to archiving and analysing group and individual patient data on associations between genotypes and drug-response phenotypes. Here, we discuss the rationale for such personalized medicine databases, and the key practical and ethical issues that need to be addressed in their establishment.

(7) Jorgensen, J T; *From blockbuster medicine to personalized medicine*

Journal: Personalized medicine ISSN: 1741-0541, Date: 2008 Volume: 5 Issue: 1 Page: 55:

One of the biggest challenges for the biotechnology and pharmaceutical companies in the 21st century will be to develop and deliver drugs that fit the individual patient's biology and pathophysiology. This change from blockbuster medicine to personalized medicine will, to a large extent, influence the way that drugs are going to be developed, marketed and prescribed in the future. These changes could mean an end to the blockbuster philosophy in 'big pharma' and thereby impose major changes in company structures. The implementation of personalized medicine will be a stepwise process, where the division of patients into biological subgroups will be the first important step. Today, this is already the situation for several cancer diseases, for example, breast cancer. In the years to come, we will see more and more drugs being prescribed based on the results from pharmacodiagnostic testing. Within cancer medicine, which has been at the forefront of this field, it is expected that in 10-15 years time very few drugs will be prescribed without such a test. 2008 Future Medicine Ltd.

Specific References

Biowulf Technologies, Llc, Pre-processed Feature Ranking for a support Vector Machine, WO2003040949, US20050131847A1, EP1449108, Priority date 2001, Nov. 7

Defoin-Platel, M., S. Schliebs, et al. (2007). A versatile quantum inspired evolutionary algorithm. *IEEE Congress on Evolutionary Computation*. Singapore, IEEE Press.

Defoin-Platel, M., S. Schliebs, at al. (2008). "Quantum-inspired Evolutionary Algorithm: A multi-model EDA" *IEEE Trans. Evolutionary Computation* to appear Goldberg, D. E. (1989). *Genetic Algorithms in Search, Optimization and machine Learning*. Reading, Mass., Addison-Wesley.

Kasabov, N. (2000) ADAPTIVE LEARNING SYSTEM AND METHOD, WO2001078003, US2003149676, EP1287488, NZ503882, AU52793/01, U.S. Pat. No. 7,089,217, University of Otago, Priority date 2000 Apr. 10

Kasabov, N. (2007). *Evolving Connectionist Systems: The Knowledge Engineering Approach*. London, Springer.

Kasabov, N. (2007). "Global, local and personalised modelling and profile discovery in Bioinform/atics: An integrated approach." *Pattern Recognition Letters* Vol. 28(6, April): 673-685

Kasabov, N. K. (2002). *Evolving Connectionist Systems. Methods and Applications in Bioinformatics, Brain Study and Intelligent Machines*. London, Springer-Verlag.

Kasabov, N., L. Goh and M. Sullivan, Integrated Prognostic Profiles: Combining Clinical and Gene Expression Information through Evolving Connectionist Approach, Chapter 10, in: V. Bajic and Tan Tin Wee (eds), Inform. Process. and Living Systems, Imp. College Press, Sing, 2005, 695-706

Mohan, N. and N. Kasabov, Transductive Modelling with GA parameter optimisation. IJCNN 2005 Conf. Proceed., IEEE Press, 2005, Volume 2, pp 839-844

Song, Q. and N. Kasabov (2006). "TWNFI—a transductive neuro-fuzzy inference system with weighted data normalisation for personalised modelling." *Neural Networks* 19(10): 1591-1596.

Vapnik, V. (1998). *Statistical Learning Theory*, John Wiley & Sons, Inc.

van Veer, L. J. v. t., Dai, H., Vijver, M. J. v. d., He, Y. D. & et al. (2002) Nature 415, 530.

G. F. Gates, "Creatinine clearance estimation from serum creatinine values: An analysis of three mathematical models of glomerular function", *American Journal of Kidney Diseases* vol. 5, pp. 199-205, 1985

A. S. Levey, J. P. Bosch, J. B. Lewis, T. Greene, N. Rogers, D. Roth, for the Modification of Diet in Renal Disease Study Group, "A More Accurate Method To Estimate Glomerular Filtration Rate from Serum Creatinine: A New Prediction Equation", Annals of Internal Medicine, vol. 130, pp. 461-470, 1999.

M. Marshall, Q. Song, T M. Ma, S. MacDonell and N. Kasabov, "Evolving Connectionist System versus Algebraic Formulae for Prediction of Renal Function from Serum Creatinine", *Kidney International*, 67, 1944-1954, 2005

Nevins, J R, Towards integrated clinico-genomic models for personalized medicine: combining gene expression signatures and clinical factors in breast cancer outcomes prediction, Journal: Human molecular genetics, ISSN: 0964-6906, Date: 2003, Volume: 12, Issue: 90002, Page: 153R Sureka, Ashish, Automated Predictive Data Mining Model Selection, US Patent 20080077544A1

What I claim is:

1. A computer implemented method of optimizing a transductive model Mx suitable for use in data analysis and determining a prognostic outcome specific to a particular subject x represented as input vector x, wherein input vector x comprises a number of variable features in relation to a scenario of interest for which there is a global dataset D of samples also having the same variable features relating to the scenario as input vector x, and for which an outcome is known, the method comprising:

(A) optimizing the transductive model by:
a) determining what number and a subset Vx of variable features of input vector x will be used in assessing an outcome for the input vector x;
b) determining what number Kx of samples from within the global data set D will form a neighborhood about input vector x;
c) selecting suitable Kx samples from the global data set which have the variable features that most closely accord to the variable features of the particular subject x to form the neighborhood Dx;
d) ranking the Vx variable features within the neighborhood Dx in order of importance to the outcome and obtaining a weight vector Wx for all variable features Vx;
e) creating a prognostic transductive model Mx for each input vector x, having a set of model parameters Px and the other parameters Vx and Kx from elements a)-d);
f) testing an accuracy of the model Mx for each sample from Dx method selected from the group consisting of:
(i) calculating Wx as normalized SNR (Signal-to-Noise Ratio) coefficients and sorting the variables in descending order: V1, V2, . . . , Vv, where: w1>=w2>= . . . >=wy, calculated as follows:

$$w_1 = abs(M1^{(class\ 1,x)} - M1^{(class\ 2,x)})/(Std1^{(class1)} + Std1^{(class2)});$$

(ii) testing for all variables Vx all possible combinations of values of their weights Wx are tested through an exhaustive search to maximize the overall accuracy of a model built on the data Dx;
(iii) applying a genetic statistical analysis procedure, if the number of variables prevents using method (ii) above;
(iv) applying a quantum inspired evolutionary statistical analysis technique, to select the optimal variable set Vx for every new input vector x and to weigh the variables through a probability wave function;
g) storing both the accuracy and the set of model parameters;
h) repeating elements a) and/or b) while applying an optimization procedure to optimize Vx and/or Kx, to determine their optimal values, before repeating elements c)-h) until the accuracy is maximized, wherein a number and a subset Vx of variable features of input vector x, and a number Kx of samples from within the global data set D that form a neighborhood about input vector x are determined anew each time elements a) and b) are repeated while applying an optimization procedure to optimize Vx and/or Kx;

(B) determining a prognostic outcome y specific to the patient x using the optimized transductive model Mx by:

(I) forming a vector: Fx={Vx,Wx,Kx,Dx,Mx,Px,t}, where the variable t represents the time of the model Mx creation;

(II) calculating the weighted distance D(Fx,Fd) as an aggregated indication of how much a person's profile should change to reach an average desired profile Fd by using the following:

$$D(Fx,Fd)=\Sigma_{l=1,v} abs(V_{lx}-V_{ld}) \cdot w_l;$$

(III) designing a vector of required variable changes, defined as: deltaFx,d=(deltaV$_{lx,d}$), for l=1,v as follows: deltaV$_{lx,d}$=V$_{lx}$−V$_{ld}$, with an importance of: Wl;

(C) modifying variable features Vx in the patient x to be closer to Kx values associated with an improved outcome relative to the prognostic outcome y determined for the patient x so as to improve the prognostic outcome of the patient x; and (D) repeating elements a) through h) to determine an improved prognostic outcome using re-optimized transductive model Mx.

2. The method as claimed in claim 1 further comprising:
i) calculating the outcome y for the input vector x using the optimized transductive model Mx.

3. The method as claimed in claim 2, wherein optimizing the transductive model further comprises:
j) profiling input vector x and comparing important variable features against important variable features associated with a desired outcome to provide for, or assist with, development of, scenarios for improvement of the outcome for input vector x.

4. A computer system which includes:
a hardware comprising, a processor and associated memory;
the system characterized in that the hardware has been programmed to:
access a global dataset of samples relating to a scenario of interest, and for which an outcome is known, each sample having a number of variable features, which may or may not relate to the scenario;
receive input information relating to an input vector x; and
to perform a method as claimed in claim 1.

5. A non-transitory computer memory medium which contains a program which is capable of performing a method as claimed in claim 1 on a global dataset of samples for which an outcome is known relating to a scenario of interest, each sample having a number of variable features, which may or may not relate to the scenario; and wherein the program provides for a user interface to receive input information relating to an input vector x and wherein the program also provides graphic display of one or more method results.

6. The method as claimed in claim 1, wherein the prognostic transductive model Mx is a personalized model.

7. The method as claimed in claim 6, wherein the personalized model is a unique personalized model.

8. The method as claimed in claim 1, wherein the scenario for which an outcome is known comprises at least two different known outcomes.

9. The method as claimed in claim 1, wherein the scenario for which an outcome is known comprises at least two different scenarios.

10. The method as claimed in claim 1, wherein a known outcome is associated with each sample in the global dataset and determined neighborhood.

11. The method as claimed in claim 1, wherein the global dataset has samples having one of at least two different outcomes, wherein a particular outcome for each sample is known.

12. The method as claimed in claim 1, wherein new data is compared with accumulated existing data samples for which a future outcome is known for each sample.

13. A computer implemented method of improving a personal outcome for a particular subject x having a prognostic outcome, the method comprising:

(A) optimizing a transductive model by:
a) determining what number and a subset Vx of variable features of input vector x will be used in assessing an outcome for the input vector x;
b) determining what number Kx of samples from within the global data set D will form a neighborhood about input vector x;
c) selecting suitable Kx samples from the global data set which have the variable features that most closely accord to the variable features of the particular subject x to form the neighborhood Dx;
d) ranking the Vx variable features within the neighborhood Dx in order of importance to the outcome and obtaining a weight vector Wx for all variable features Vx;
e) creating a prognostic transductive model Mx for each input vector x, having a set of model parameters Px and the other parameters Vx and Kx from elements a)-d);
f) testing an accuracy of the model Mx for each sample from Dx method selected from the group consisting of:
(i) calculating Wx as normalized SNR (Signal-to-Noise Ratio) coefficients and sorting the variables in descending order: V1,V2, . . . ,Vv, where: w1>=w2>= . . . >=wy, calculated as follows:

$$w_1 = abs(M1^{(class\ 1,x)} - M1^{(class\ 2,x)})/(Std1^{(class1)} + Std1^{(class2)});$$

(ii) testing for all variables Vx all possible combinations of values of their weights Wx are tested through an exhaustive search to maximize the overall accuracy of a model built on the data Dx;
(iii) applying a genetic statistical analysis procedure, if the number of variables prevents using method (ii) above;
(iv) applying a quantum inspired evolutionary statistical analysis technique, to select the optimal variable set Vx for every new input vector x and to weigh the variables through a probability wave function;
g) storing both the accuracy and the set of model parameters;
h) repeating elements a) and/or b) while applying an optimization procedure to optimize Vx and/or Kx, to determine their optimal values, before repeating elements c)-h) until the accuracy is maximized, wherein a number and a subset Vx of variable features of input vector x, and a number Kx of samples from within the global data set D that form a neighborhood about input vector x are determined anew each time elements a) and b) are repeated while applying an optimization procedure to optimize Vx and/or Kx;

(B) determining a prognostic outcome y specific to the patient x using the optimized transductive model Mx by:
(I) forming a vector: Fx={Vx,Wx,Kx,Dx,Mx,Px,t}, where the variable t represents the time of the model Mx creation;
(II) calculating the weighted distance D(Fx,Fd) as an aggregated indication of how much a person's profile should change to reach an average desired profile Fd by using the following:

$$D(Fx,Fd)=\Sigma_{l=1,v}abs(V_{lx}-V_{ld})\cdot w_l;$$

(III) designing a vector of required variable changes, defined as: deltaFx,d, (deltaV$_{lx,d}$), for l=1,v as follows: deltaV$_{lx,d}$=V$_{lx}$−V$_{ld}$, with an importance of: Wl;
(C) modifying variable features Vx in the patient x to be closer to Kx values associated with an improved outcome relative to the prognostic outcome y determined for the patient x so as to improve the prognostic outcome of the patient x; and
(D) repeating elements a) through h) to determine an improved prognostic outcome using re-optimized transductive model Mx.

14. The method as claimed in claim 13, wherein one or more variable features of input vector x are selected as incapable of being altered for step (III).

15. The method as claimed in claim 13, wherein step (C) comprises administration of a drug.

* * * * *

UNITED STATES PATENT AND TRADEMARK OFFICE
CERTIFICATE OF CORRECTION

PATENT NO. : 9,002,682 B2
APPLICATION NO. : 13/088306
DATED : April 7, 2015
INVENTOR(S) : Nikola Kirilov Kasabov It is certified that error appears in the above-identified patent and that said Letters Patent is hereby corrected as shown below:

In The Specification

In column 1 at lines 12-17 (approx.), Delete "PCT/NZ2009/000222 also claimed….incorporated by reference." and insert the same on Col. 1, Line 13 (approx.) as a new paragraph.

In column 1 at line 32, Change "ref" to --ref.--.

In column 3 at line 8, Change "$(x_i,y_j)$" to --$(x_j,y_j)$--.

In column 3 at line 45, Change "form" to --for a--.

In column 7 at line 3, Change "(FIG.2)," to --(FIG.2).--.

In column 7 at line 50, Change "population h" to --population h.--.

In column 7 at line 51, Change "mutation h" to --mutation h.--.

In column 9 at lines 12-13 (approx.), Change

"$$w_I = abs(M_I^{(class\ 1,x)} - M_I^{(class\ 2,x)})/(Std_I^{(class1)} + Std_I^{class2})$$" to --$$w_I = abs(M_I^{(class\ 1,x)} - M_I^{(class\ 2,x)})/(Std_I^{(class1)} + Std_I^{(class2)})$$--.

In column 9 at line 47, Change "neigbourhood" to --neighbourhood--.

In column 9 at line 66, Change "example;" to --example:--.

Signed and Sealed this
Fifth Day of April, 2016

Michelle K. Lee
*Director of the United States Patent and Trademark Office*

CERTIFICATE OF CORRECTION (continued)
U.S. Pat. No. 9,002,682 B2

In column 10 at line 67 (approx.), Change

"$d_j = \text{sqr}[\text{sum}_{l=1 \text{ to } v}(w_l(x_l =_{jl}))^2]$," to

--$d_j = \text{sqr}[\text{sum}_{l=1 \text{ to } v}(w_l(x_l - x_{jl}))^2]$,--.

In column 11 at line 60, Change

"$D(Fx, Fi) = \Sigma_{l=1,v} abs(V_{lx} - V_{li}) \cdot w_l$" to

--$D(Fx, Fi) = \Sigma_{l=1,v} abs(V_{lx} - V_{li}) \cdot w_l$--.

In column 11 at line 66 (approx.), Change

"$D(Fx, Fd) = \Sigma_{l=1,v} abs(V_{lx} - V_{ld}) \cdot w_l$" to

--$D(Fx, Fd) = \Sigma_{l=1,v} abs(V_{lx} - V_{ld}) \cdot w_l$--.

In column 13 at line 14, Change "disease Example" to --disease from the whole data set (wtccc.org) in the WTCCC project (see Example--.

In column 13 at line 17, Change "at al," to --et al,--.

In column 13 at line 51, Change "gender." to --gender,--.

In column 14 at line 58, Change "than" to --then--.

In column 14 at line 66, Change "interations" to --interactions--.

In column 15 at line 30, Change "net" to --set--.

In column 15 at line 62, Change "KNN" to --WWKNN--.

In column 15 at line 64, Change "KNN" to --WWKNN--.

In column 19 at line 34, Change "Austria" to --Austria.--.

In column 19 at line 46, Change "personlised" to --personalised--.

In column 20 at line 1, Change "(II):" to --(11):--.

In column 21 at line 22, Change "(genes)" to --(genes).--.

In column 23 at line 56, Change "2007))." to --2007).--.

In column 25 at line 20, Change "WKNN" to --kNN--.

In column 25 at line 22, Change "peronsalised" to --personalised--.

In column 25 at line 60, Change "web site." to --website.--.

In column 25 at line 67, Change "web site." to --website.--.

In column 27 at line 11 (approx.), Change "test." to --test. ©--.

In column 27 at line 16, Change "Llc," to --LLC,--.

In column 27 at lines 19-20 (approx.), Change "Nov 7" to --Nov. 7.--.

In column 27 at line 24, Change "at al." to --et al.--

In column 27 at line 26, Change "appear" to --appear.--.

In column 27 at line 33 (approx.), Change "Apr. 10" to --Apr. 10.--.

In column 27 at line 38 (approx.), Change "Bioinform/atics:" to --Bioinformatics:--.

In column 27 at line 40 (approx.), Change "673-685" to --673-685.--.

In column 27 at lines 48-49, Change "695-706" Lu --695-706.--.

In column 27 at line 51, Change "optimisation." to --optimisation,--.

In column 27 at line 52, Change "839-844" to --839-844.--.

In column 27 at line 64, Change "1985" to --1985.--.

In column 28 at line 7, Change "2005" to --2005.--.

In column 28 at line 12, Change "153R" to --153R.--.

In column 28 at line 14, Change "20080077544A1" to --20080077544A1.--.

In The Claims

In column 31 at line 12, In Claim 13, change "deltaFx,d, (deltaV$_{lx,d}$)," to --deltaFx,d=(deltaV$_{lx,d}$),--.